US010537277B2

United States Patent
Wu et al.

(10) Patent No.: US 10,537,277 B2
(45) Date of Patent: Jan. 21, 2020

(54) METHODS, SYSTEMS, AND COMPUTER READABLE MEDIA FOR VISUALIZATION OF RESECTION TARGET DURING EPILEPSY SURGERY AND FOR REAL TIME SPATIOTEMPORAL VISUALIZATION OF NEUROPHYSIOLOGIC BIOMARKERS

(71) Applicants: The Trustees of the University of Pennsylvania, Philadelphia, PA (US); THOMAS JEFFERSON UNIVERSITY HOSPITALS, INC., Philadelphia, PA (US)

(72) Inventors: Chengyuan Wu, Merion, PA (US); Allan Azarion, Potomac, MD (US); Jue Wu, Pittsburgh, PA (US); Ankit N. Khambhati, West Windsor, NJ (US); Joost Wagenaar, Rutledge, PA (US); Brian Litt, Bala Cynwyd, PA (US); Justin Blanco, Annapolis, MD (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 884 days.

(21) Appl. No.: 14/894,819

(22) PCT Filed: May 28, 2014

(86) PCT No.: PCT/US2014/039865
§ 371 (c)(1),
(2) Date: Nov. 30, 2015

(87) PCT Pub. No.: WO2014/194006
PCT Pub. Date: Dec. 4, 2014

(65) Prior Publication Data
US 2016/0120457 A1 May 5, 2016

Related U.S. Application Data

(60) Provisional application No. 61/828,173, filed on May 28, 2013, provisional application No. 61/828,168, filed on May 28, 2013.

(51) Int. Cl.
*A61B 5/00* (2006.01)
*A61B 5/04* (2006.01)
(Continued)

(52) U.S. Cl.
CPC ........ *A61B 5/4094* (2013.01); *A61B 5/04012* (2013.01); *A61B 5/0478* (2013.01);
(Continued)

(58) Field of Classification Search
CPC . A61B 5/04012; A61B 5/0476; A61B 5/0478; A61B 5/055; A61B 5/4094;
(Continued)

(56) References Cited

U.S. PATENT DOCUMENTS 5,438,989 A 8/1995 Hochman et al.
5,848,967 A 12/1998 Cosman
(Continued)

FOREIGN PATENT DOCUMENTS

EP    1 554 987 B1    3/2009

OTHER PUBLICATIONS

Notification of Transmittal of the International Search Report and the Written Opinion of the International Searching Authority, or the Declaration for International Application No. PCT/US2014/039865 (dated Oct. 20, 2014).

(Continued)

*Primary Examiner* — Ruth S Smith
(74) *Attorney, Agent, or Firm* — Jenkins, Wilson, Taylor & Hunt, P.A.

(57) ABSTRACT

The subject matter described herein relates to methods, systems, and computer readable media for visualization of a resection target during epilepsy surgery and for real time spatiotemporal visualization of neurophysiologic biomarkers. One exemplary method includes a real time neurophysiologic biomarker visualization system implemented by at (Continued)

least one computer, receiving, as input, a pre-electrode-implantation MRI of an epilepsy patient's brain.

36 Claims, 13 Drawing Sheets

(51) Int. Cl.
    *A61B 5/0478*     (2006.01)
    *G01R 33/48*     (2006.01)

(52) U.S. Cl.
    CPC .......... *A61B 5/4836* (2013.01); *A61B 5/7435* (2013.01); *G01R 33/4806* (2013.01); *G01R 33/4812* (2013.01)

(58) Field of Classification Search
    CPC ... A61B 5/4836; A61B 5/6868; A61B 5/7425; A61B 5/7435; G01R 33/4806; G01R 33/4812
    See application file for complete search history.

(56) References Cited

U.S. PATENT DOCUMENTS

| | | | |
|---|---|---|---|
| 6,035,228 | A | 3/2000 | Yanof et al. |
| 6,070,098 | A | 5/2000 | Moore-Ede et al. |
| 6,351,659 | B1 | 2/2002 | Vilsmeier |
| 6,351,661 | B1 | 2/2002 | Cosman |
| 6,859,660 | B2 | 2/2005 | Vilsmeier |
| 7,216,001 | B2 | 5/2007 | Hacker et al. |
| 7,558,617 | B2 | 7/2009 | Vilsmeier |
| 8,065,011 | B2 | 11/2011 | Echauz et al. |
| 8,934,965 | B2 | 1/2015 | Rogers et al. |
| 9,326,698 | B2 | 5/2016 | Blanco et al. |
| 2003/0158587 | A1 | 8/2003 | Esteller et al. |
| 2005/0148859 | A1 | 7/2005 | Miga et al. |
| 2007/0225674 | A1 | 9/2007 | Molnar et al. |
| 2009/0118635 | A1 | 5/2009 | Lujan et al. |
| 2009/0220136 | A1 | 9/2009 | Bova et al. |
| 2010/0098289 | A1 | 4/2010 | Tognoli et al. |
| 2012/0245481 | A1 | 9/2012 | Blanco et al. |
| 2012/0271151 | A1 | 10/2012 | LaVoilette et al. |
| 2013/0072775 | A1 | 3/2013 | Rogers et al. |
| 2015/0080695 | A1 | 3/2015 | Rogers et al. |

OTHER PUBLICATIONS

Maes et al., "Multi-modality image registration by maximization of mutual information," pp. 14-22 (1996). (Retrieved from https://mirc.uzleuven.be/download/public/MIC/publications/976/paper.pdf Jun. 13, 2016).
Nuwer et al., "IFCN standards for digital recording of clinical EEG," Electoencephalography and Clinical Neurophysiology, 106 (3): 259-261 (1998).
Silberbusch et al., "Subdural grid implantation for intracranial EEG recording: CT and MR appearance," Am J Neuroradiol 19(6): 1089-1093 (1998).
Kwan et al., "Epilepsy after the first drug fails: substitution or add-on?" Seizure 9(7), 464-468 (2000).
Wiebe et al., "A randomized, controlled trial of surgery for temporal-lobe epilepsy," N Eng! J Me/d. 2;345(5):311-318.
Skrinjar et al., "Model-driven brain shift compensation," Med Image Anal, (4): 361-373 (2002).
Smith, "Fast robust automated brain extraction," Human Brain Mapping, 17(3): 143-155 (2002).
Staba et al., "Quantitative analysis of high-frequency oscillations (80-500Hz) recorded in human epileptic hippocampus and entorhinal cortex," Journal of Neurophysiology, 88(4): 1743-1752 (2002).
Wellmer et al., "Digital photography and 3D MRI-based multimodal imaging for individualized planning of respective neocortical epilepsy surgery," Epilepsia 43(12): 1543-1550 (2002).
Schulze-Bonhage et al., "Visualization of subdural strip and grid electrodes using curvilinear reformatting of 3D MR imaging data sets," Am J Neurodariol 23(3): 400-403 (2002).
Engel et al., "Practice parameter: temporal lobe and localized neocortical resections for epilepsy," Neurology 2003, 60:538-547 (2003).
Finnis et al., "Three-dimensional database of subcortical electrophysiology for image-guided stereotactic functional neurosurgery," IEEE Transactions on Medical Imaging 22(1):93-104 (Jan. 2003).
Asano et al., "Is Intraoperative Electrocorticography Reliable in Children with Intractable Neocortical Epilepsy?" Epilepsia, 45(9): 1091-1099 (2004).
Hastreiter et al., "Strategies for brain shift evaluation," Med Image Anal. 8(4): 447-464 (2004).
Morris et al., "A computer-generated stereotactic 'Virtual Subdural Grid' to guide respective epilepsy surgery," Am J Neuroradiol 25(1):77-83 (2004).
Nelles et al., "Fusion of MRI and CT with subdural grid electrodes," Zentralbl Neurochir 65(4): 17 4-9 (2004).
Worrell et al., "High-frequency oscillations and seizure generation in neocortical epilepsy," Brain, 127: 1496-1506 (Jul. 2004).
Yushkevich et al., "User-guided 3D active contour segmentation of anatomical structures: Significantly improved efficiency and reliability," Neuroimage, 31(3), 1116-1128 (2006).
Ding et al., "EEG source imaging: Correlate source locations and extents with ECoG and surgical resections in epilepsy patients," Journal of Clinical Neurophysiology 130-136 (2007).
Dalai et al., "Localization of neurosurgically implanted electrodes via photograph-MRI-radiograph coregistration," J Neurosci Methods 15;174(1): 106-115 (2008).
Choi et al., "Epilepsy Surgery for Pharmacoresistant Temporal Lobe Epilepsy," Journal of American Medical Association, 300 (21)2497-2505 (2008).
Joshi et al., "Novel interaction techniques for neurosurgical planning and stereotactic navigation," IEEE Transactions on Visualization and Computer Graphics, 14(6): 1587-1594 (2008).
Worrell et al., "High-frequency oscillations in human temporal lobe: simultaneous microwire and clinical macroelectrode recordings," Brain, 131(Pt 4):928-937 (2008).
Klein et al., "Evaluation of 14 nonlinear deformation algorithms applied to human brain MRI registration," Neuroimage 46, 786-802 (2009).
Schevon et al., "Spatial characterization of interictal high frequency oscillations in epileptic neocortex," Brain, 132 (11): 3047-3059 (Nov. 2009).
Ortler et al., "Integration of multimodality imaging and surgical navigation in the management of patients with refractory epilepsy. A pilot study using a new minimally invasive reference and head-fixation system," Acta neurochirurgica, 152(2): 365-78 (Feb. 2010).
Blanco et al., "Unsupervised classification of high-frequency oscillations in human neocortical epilepsy and control patients," Journal of Neurophysiology 104(5):2900-2912 (Nov. 2010).
Wang et al., "Fusion and visualization of intraoperative cortical images with preoperative models for epilepsy surgical planning and guidance," Computer Aided Surgery, 16(4): 149-160 (2011).
Akiyama et al., "Topographic movie of intracranial ictal high-frequency oscillations with seizure semiology; epileptic network in Jacksonian seizures," Epilepsia, 52(1): 75-83 (2011).
Wilson et al.,"Massively Parallel Signal Processing using the Graphics Processing Unit for Real-Time Brain-Computer Interface Feature Extraction," Frontiers in Neuroengineering, 2(July): 11 (Jan. 2009).
Fong et al., "Seizure outcome and its predictors after temporal lobe epilepsy surgery in patients with normal MRI," Epilepsia, 52 (8): 1393-1401 (Aug. 2011).
Blanco et al., "Data mining neocortical high-frequency oscillations in epilepsy and controls," Brain, 134 (Pt 10): 2948-59 (Oct. 2011).
Tisi et al., "The long-term outcome of adult epilepsy surgery, patterns of seizure remission, and relapse: a cohort study," Lancet, 378:1388-1395 (Oct. 2011).
Viventi et al., "Flexible, foldable actively multiplexed, highdensity electrode array for mapping brain activity in vivo," Nature Neuroscience 14)12) 1599-1605 (Nov. 2011).

(56) References Cited

OTHER PUBLICATIONS

Dykstra et al., "lndividualilzed localization and cortical surface-based registration of intracranial electrodes," Neuroimage 15; 59(4) 3563-3570 (2012).
Zijlmans et al., "High-frequency oscillations as a new biomarker in epilepsy," Annals of Neurology, 71(2): 169-78 (Feb. 2012).
Worrell et al., "Recording and analysis techniques for high-frequency oscillations," Progress in Neurobiology (Mar. 2012).
Pieters et al., "Recursive grid partitioning on a cortical surface model: an optimized technique for the localization of implanted subdural electrodes," J Neurosurg (Mar. 15, 2013).
Barreto et al., "An on-line system for intraoperative focus localization from array electrocorticography," In Proceedings of the 1994 IEEE, vol. C, pp. 418-422 (1994).
Dimitrov, "Texturing 3D-Reconstructions of the Human Brain with EEG-Activity Maps," Human Brain Mapping, vol. 6, No. 4, pp. 189-202 (Jan. 1998).
Winkler et al., "Usefulness of 3-D reconstructed images of the human cerebral cortex for localization of subdural electrodes in epilepsy surgery," Epilepsy Reseach, vol. 41, No. 2, pp. 169-178 (2000).
Studholme et al., "Estimating Tissue Deformation between Functional Images Induced by Intracranial Electrode Implantation Using Anatomical MRI," Neuroimage, vol. 13, No. 4, pp. 561-576 (2001).
Hamer et al., "Complications of invasive video-EEG monitoring with subdural grid electrodes," Neurology, vol. 58, No. 1, pp. 97-103 (Jan. 2002).
Immonen et al., "3-D reconstructed magnetic resonance imaging in localization of subdural EEG electrodes Case illustration," Epilepsy Research, vol. 54, No. 1, pp. 59-62 (2003).
Nelles et al., "Fusion of MRI and CT with Subdural Grid Electrodes," Zentralbl Neurochir, vol. 65, No. 4, pp. 174-179 (2004).
Siegel, "Presurgical evaluation and surgical treatment of medically refractory epilepsy," Neurosurgical Review, vol. 27, pp. 1-18 (Jan. 2004).
Hunter et al., "Locating chronically implanted subdural electrodes using surface reconstruction," Clinical Neurophysiology, vol. 116, No. 8, pp. 1984-1987 (2005).
Kovalev et al., "Rapid and Fully Automated Visualization of Subdural Electrodes in the Presurgical Evaluation of Epilepsy Patients," American Journal of Neuroradiology, vol. 26, No. 5, pp. 1078-1083 (May 2005).
Akiyama et al., "Topographic Movie of Ictal High-Frequency Oscillations on the Brain Surface Using Subdural EEG in Neocortical Epilepsy," Epilepsia, vol. 47, No. 11, pp. 1953-1957 (2006).
Sebastiano et al., "A rapid and reliable procedure to localize subdural electrodes in presurgical evaluation of patients with drug-resistant focal epilepsy," Clinical Neurophysiology, vol. 117, No. 2, pp. 341-347 (2006).
Christensen et al., "Introduction to the Non-Rigid Image Registration Evaluation Project (NIREP)," Biomedical Image Registration, Third International Workshop, pp. 128-135 (2006).
Elias et al., "Cortical and subcortical brain shift during sterotactic procedures," J, Neurosurg., vol. 107, No. 5, pp. 983-988 (Nov. 2007).
Ken et al., "Quantitative evaluation for brain CT/MRI coregistration based on maximiazation of mutual information in patients with focal epilepsy investigated with subdural electrodes," Magnetic Resonance Imaging, vol. 25, pp. 883-888 (2007).
Urrestarazu et al., "Interictal high-frequency oscillations (100-500 Hz) in the intracerebral EEG of epileptic patients," Brain, vol. 130, pp. 2354-2366 (Sep. 2007).
Tao et al., "The accuracy and reliability of 3D CT/MRI co-registration in planning epilepsy surgery," Clinical Neurophysiology, vol. 120, No. 4, pp. 748-753 (2009).
Im et al., "EEG-based Real-time Dynamic Neuroimaging," 31st Annual International Conference of the IEEE EMBS, pp. 5385-5388 (Sep. 2009).

Wang et al., "Fusion of Intraoperative Cortical Images with Preoperative Models for Neurosurgical Planning and Guidance," Proceedings of SPIE, vol. 7261, pp. 1-8 (2009).
Wang et al., "Fusion and visualization of intraoperative cortical images with preoperative models for epilepsy surgical planning and guidance," Computer Aided Surgery, vol. 16, No. 4, pp. 149-160 (Jul. 2011).
Darcey et al., "Technique for the localization of intracranially implanted electrodes," J Neurosurg, vol. 113, No. 6, pp. 1182-1185 (Dec. 2010).
Hermes et al., "Automated electrocorticographic electrode localization on individually rendered brain surfaces," Journal of Neuroscience Methods, vol. 185, No. 2, pp. 293-298 (2010).
Crépon et al., "Mapping interictal osciallations greater than 200 Hz recorded with intracranial macroelectrodes in human epilespy," vol. 133, pp. 33-45 (Jan. 2010).
Viventi et al., "Mining Terabytes of Submillimeter-resolution ECoG Datasets for Neurophysiologic Biomarkers," 32nd Annual International Conference of the IEEE EMBS, pp. 3825-3826 (2010).
Jacobs et al., "High-Frequency Electroencephalographic Oscillations Correlate with Outcome of Epilespy Surgery," Annals of Neurology, vol. 67, No. 2, pp. 209-220 (Feb. 2010).
Avants et al., "An Open Source Multivariate Framework for n-Tissue Segmentation Evaluation on Public Data," Neuroinformatics, vol. 9, No. 4, pp. 1-30 (2011).
Okonma et al., "Planning extent of resection in epilepsy: Limited versus large resections," Epilepsy and Behavior, vol. 20, No. 2, pp. 233-240 (2011).
LaViolette et al., "3D visualization of subdural electrode shift as measured at craniotomy reopening," Epilespsy Research, vol. 94, No. 1-2, pp. 1-15 (Mar. 2011).
Imamura et al., "Ictal wideband ECoG: Direct comparison between ictal slow shifts and hugh frequency oscillations," Clinical Neurophysiology, vol. 122, No. 8, pp. 1500-1504 (Aug. 2011).
Hotelling, H., "Analysis of a complex of statistical variables into principal components," The Journal of Educational Psychology, vol. 24, No. 6, pp. 417-441 (Sep. 1933).
Cohen, J., "A coefficient of agreement for nominal scales," Education and Psychological Measurement, vol. 20, No. 1, pp. 37-46 (1960).
Slepian et al., "Prolate Spheroidal Wave Functions, Fourier Analysis and Uncertainty-I," The Bell System Technical Journal, vol. 40, No. 1, pp. 43-63 (Jan. 1961).
O'Keefe, "Place Units in the Hippocampus of the Freely Moving Rat," Experimental Neurology, vol. 51, No. 1, pp. 78-109 (Apr. 1976).
Usui et al., "Digital Low-Pass Differentiation for Biological Signal Processing," IEEE Transactions on Biomedical Engineering, vol. BME-29, No. 10, pp. 686-693 (Oct. 1982).
Buzsaki et al., "Cellular bases of hippocampal EEG in the behaving rat," Brain Research, vol. 287, No. 2, pp. 139-171 (Oct. 1983).
Mallat, "A Theory for Multiresolution Signal Decomposition: The Wavelet Representation," IEEE Transactions on Pattern Analysis and Machine Intelligence, vol. 11, No. 7, pp. 674-693 (Jul. 1989).
Kaiser, "On a simple algorithm to calculate the energy of a signal," In International Conference on Acoustics, Speech, and Signal Processing, vol. 1, pp. 381-384 (Apr. 3-6, 1990).
Allen et al., "Very high-frequency rhythmic activity during SEEG suppression in frontal lobe epilepsy," Electroencephalography and Clinical Neurophysiology, vol. 82, No. 2, pp. 155-159 (Feb. 1992).
Buzsaki et al., "High-Frequency Network Oscillation in the Hippocampus," Science, vol. 256, No. 5059, pp. 1025-1027 (May 1992).
Fisher et al., "High Frequency EEG Activity at the Start of Seizures," Journal of Clinical Neurophysiology, vol. 9, No. 3, pp. 441-448 (Jul. 1992).
Vetterli et al., "Wavelets and Filter Banks: Theory and Design," IEEE Transactions on Signal Processing, vol. 40, No. 9, pp. 2207-2232 (Sep. 1992).
Wilson et al., "Reactivation of Hippocampal Ensemble Memories During Sleep," Science, vol. 265, No. 5172, pp. 676-679 (Jul. 1994).

(56) References Cited

OTHER PUBLICATIONS

Ylinen et al., "Sharp Wave-Associated High-Frequency Oscillation (200Hz) in the Intact Hippocampus: Network and Intracellular Mechanisms," The Journal of Neuroscience, vol. 15, No. 1, pp. 30-46 (Jan. 1995).
Learned et al., "A Wavelet Packet Approach to Transient Signal Classification1," Applied and Computational Harmonic Analysis, vol. 2, No. 3, pp. 265-278 (Jul. 1995).
Chrobak et al., "High-Frequency Oscillations in the Output Networks of the Hippocampal-Entorhinal Axis of the Freely Behaving Rat," The Journal of Neuroscience, vol. 16, No. 9, pp. 3056-3066 (May 1996).
Nuttall, "Near-Optimum Detection Performance of Power-Law Processors for Random Signals of Unknown Locations, Structure, Extent, and Arbitrary Strengths," Technical Report 11, 123, Naval Undersea Warfare Center Newport Division, 162 pages (Apr. 15, 1996).
Sander et al., "Epidemiology of the epilepsies," Journal of Neurology, Neurosurgery, and Psychiatry, vol. 61, No. 5, pp. 433-443 (Nov. 1996).
Draguhn et al., "Electrical coupling underlies high-frequency oscillations in the hippocampus in vitro," Nature, vol. 394, No. 6689, pp. 189-192 (Jul. 1998).
Bragin et al., "High-Frequency Oscillations in Human Brain," Hippocampus, vol. 9, No. 2, pp. 137-142 (1999).
Csicsvari et al., "Oscillatory Coupling of Hippocampal Pyramidal Cells and Interneurons in the Behaving Rat," The Journal of Neuroscience, vol. 19, No. 1, pp. 274-287 (Jan. 1999).
Traub, et al., "High-frequency population oscillations are predicted to occur in hippocampal pyramidal neuronal networks interconnected by axoaxonal gap junctions," Neuroscience, vol. 92, No. 2, pp. 407-426 (1999).
Bragin et al., "Hippocampal and Entorhinal Cortex High-Frequency Oscillations (100-500 Hz) in Human Epileptic Brain and in Kainic Acid-Treated Rats with Chronic Seizures," Epilepsia, vol. 40, No. 2, pp. 127-137 (Feb. 1999).
Mitra et al., "Analysis of Dynamic Brain Imaging Data," Biophysical Journal, vol. 76, No. 2, pp. 691-708 (Feb. 1999).
Csicsvari et al., "Fast Network Oscillations in the Hippocampal CA1 Region of the Behaving Rat," The Journal of Neuroscience, vol. 19, No. 16, RC20, 4 pages (Aug. 1999).
Curio, "Linking 600-Hz "Spikelike" EEG/MEG wavelets ("σ-Bursts") to Cellular Substrates: Concepts and Caveats," Journal of Clinical Neurophysiology, vol. 17, No. 4, pp. 377-396 (Jul. 2000).
Draguhn et al., "Ripple (~200-Hz) Oscillations in Temporal Structures," Journal of Clinical Neurophysiology, vol. 17, No. 4, pp. 361-376 (Jul. 2000).
Stein et al., "An automated drug delivery system for focal epilepsy," Epilepsy Research, vol. 39, No. 2, pp. 103-114 (Apr. 2000).
Kwan et al., "Early identification of refractory epilepsy," The New England Journal of Medicine, vol. 342, No. 5, pp. 314-319 (Feb. 2000).
Roberts, "Extreme value statistics for novelty detection in biomedical data processing," IEEE Proceedings Science, Measurement and Technology, vol. 47, pp. 363-367 (2000).
Yang et al., "Focal Cooling Rapidly Terminates Experimental Neocortical Seizures," Annals of Neurology, vol. 49, No. 6, pp. 721-726 (Jun. 2001).
Esteller et al., "Line length: An efficient feature for seizure onset detection," In Proceedings of the 23rd Annual International Conference of the IEEE Engineering in Medicine and Biology Society, vol. 2, pp. 1707-1710 (Oct. 2001).
Grenier et al., "Focal Synchronization of Ripples (80-200 Hz) in Neocortex and Their Neuronal Correlates," Journal of Neurophysiology, vol. 86, No. 4, pp. 1884-1898 (Oct. 2001).
Wang et al., "All-Purpose and Plug-In Power-Law Detectors for Transient Signals," IEEE Transactions on Signal Processing, vol. 49, No. 11, pp. 2454-2466 (Nov. 2001).
Bragin et al., "Local Generation of Fast Ripples in Epileptic Brain," The Journal of Neuroscience, vol. 22, No. 5, pp. 2012-2021 (Mar. 2002).
Bragin et al., "Interictal High-Frequency Oscillations (80-500 Hz) in the Human Epileptic Brain: Entorhinal Cortex," Annals of Neurology, vol. 52, No. 4, pp. 407-415 (Oct. 2002).
Buzsaki et al., "Hippocampal network patterns of activity in the mouse," Neuroscience, vol. 116, pp. 201-211 (2003).
Grenier et al., "Neocortical Very Fast Oscillations (Ripples, 80-200 Hz) During Seizures: Intracellular Correlates," Journal of Neurophysiology, vol. 89, No. 2, pp. 841-852 (Feb. 2003).
Traub, "Fast Oscillations and Epilepsy," Epilepsy Currents, vol. 3, No. 3, pp. 77-79 (May 2003).
Haberman et al., "Attenuation of seizures and neuronal deaths by adeno-associated virus vector galanin expression and secretion," Nature Medicine, vol. 9, No. 8, pp. 1076-1080 (Aug. 2003).
"Medtronic Announces Start of U.S. Pivotal Clinical Trial for Intercept Epilepsy Control System," http://www.epilepsycontrol.com, pp. 1-2 (Apr. 2004).
Bragin et al., "High-frequency Oscillations after Status Epilepticus: Epileptogenesis and Seizure Genesis," Epilepsia, vol. 45, No. 9, pp. 1017-1023 (Sep. 2004).
Dzhala et al., "Mechanisms of Fast Ripples in the Hippocampus," The Journal of Neuroscience, vol. 24, No. 40, pp. 8896-8906 (Oct. 2004).
"SANTE—Stimulation of the anterior nucleus of the thalamus for epilepsy," http://clinicaltrials.gov/ct/show/NCT00101933, 4 pages (Jan. 18, 2005).
Osorio et al., "Automated Seizure Abatement in Humans Using Electrical Stimulation," Annals of Neurology, vol. 57, No. 2, pp. 258-268 (Feb. 2005).
Khosravani et al., "Increased high-frequency Oscillations Precede in vitro Low Mg2+ Seizures," Epilepsia, vol. 46, No. 8, pp. 1188-1197 (Aug. 2005).
Akiyama et al., "Focal cortical high-frequency oscillations trigger epileptic spasms: Confirmation by digital video subdural EEG," Clincal Neurophysiology, vol. 116, pp. 2819-2825 (Oct. 2005).
Barkley et al., "Safety and preliminary efficacy of the RNS™ responsive neurostimulator for the treatment of intractable epilepsy in adults," American Epilepsy Society Abstracts, p. 1 (2006).
Jirsch et al., "High-frequency oscillations during human focal seizures," Brain, vol. 129 (Pt. 6), pp. 1593-1608 (Jun. 2006).
Mölle et al., "Hippocampal Sharp Wave-Ripples Linked to Slow Oscillations in Rat Slow-Wave Sleep," J Neurophysiol, vol. 96, No. 1, pp. 62-70 (Jul. 2006).
Urrestarazu et al., "High-Frequency Intracerebral EEG Activity (100-500 Hz) Following Interictal Spikes," Epilepsia, vol. 47, No. 9, pp. 1465-1476 (Sep. 2006).
Urasaki et al., "Effects of General Anesthesia on High-Frequency Oscillations in Somatosensory Evoked Potentials," Journal of Clinical Neurophysiology, vol. 23, No. 5, pp. 426-430 (Oct. 2006).
Rampp et al., "Fast activity as a surrogate marker of epileptic network function?," Clinical Neurophysiology, vol. 117, No. 10, pp. 2111-2117 (2006).
Cimatti et al., "Time-frequency analysis reveals decreased high-frequency oscillations in writer's cramp," Brain, vol. 130, pp. 198-205 (Jan. 2007).
Joo et al., "Antiepileptic effects of low-frequency repetitive transcranial magnetic stimulation by different stimulation durations and locations," Clinical Neurophysiology, vol. 118, No. 3, pp. 702-708 (Mar. 2007).
Gardner et al., "Human and Automated Detection of High-Frequency Oscillations in Clinical Intracranial EEG Recordings," Clinical Neurophysiology, vol. 118, No. 5, pp. 1134-1143 (May 2007).
Clemens et al., "Temporal coupling of parahippocampal ripples, sleep spindles and slow oscillations in humans," Brain, pp. 1-11 (Jul. 2007).
Foffani et al., "Reduced Spike-Timing Reliability Correlates with the Emergence of Fast Ripples in the Rat Epileptic Hippocampus," Neuron, vol. 55, No. 6, pp. 930-941 (Sep. 2007).
Staley, "Neurons Skip a Beat during Fast Ripples," Neuron, vol. 55, pp. 828-830 (Sep. 20, 2007).

(56) References Cited

OTHER PUBLICATIONS

Staba et al., "Increased Fast Ripple to Ripple Rations Correlate with Reduced Hippocampal Volumes and Neuron Loss in Temporal Love Epilepsy Patients," Epilepsia, vol. 48, No. 11, pp. 2130-2138 (Nov. 2007).
Jacobs et al., "Interictal high-frequency oscillations (80-500 Hz) are an indicator of seizure onset areas independent of spikes in the human epileptic brain," Epilepsia, vol. 49, No. 11, pp. 1893-1907 (Nov. 2008).
Van Gompel et al., "Phase I trial: safety and feasibility of intracranial electroencephalography using hybrid subdural electrodes containing macro- and microelectrode arrays," Neurosurgical Focus, vol. 25, No. 3:E23, pp. 1-6 (Sep. 2008).
Kramer et al., "Sharp edge artifacts and spurious coupling in EEG frequency comodulation measures," Journal of Neuroscience Methods, vol. 170, No. 2, pp. 352-357 (May 30, 2008).
Stacey et al., "Technology Insight: Neuroengineering and epilepsy-designing devices for seizure control," Nature Clinical Practice Neurology, vol. 4, No. 4, pp. 190-201 (Apr. 2008).
Tanriverdi et al., "Long-term seizure outcome after mesial temporal lobe epilepsy surgery: corticalamygdalohippocampectomy versus selective amygdalohippocampectomy," Journal of Neurosurgery, vol. 108, No. 3, pp. 517-524 (Mar. 2008).
Bien et al., "Characteristics and Surgical Outcomes of Patients With Refractory Magnetic Resonance Imaging-Negative Epilepsies," Archives of Neurology, vol. 66, No. 12, pp. 1491-1499 (Dec. 2009).
Stacey et al., "Synaptic Noise and Physiological Coupling Generate High-Frequency Oscillations in a Hippocampal Computational Model," J Neurophysiol, vol. 102, No. 4, pp. 2342-2357 (2009).
Zijlmans et al., "High frequency oscillations and seizure frequency in patients with focal epilepsy," Epilepsy Research, vol. 85, pp. 287-292 (Aug. 2009).
Jacobs et al., "High frequency oscillations (80-500 Hz) in the preictal period in patients with focal seizures," Epilepsia, vol. 50, No. 7, pp. 1780-1792 (Jul. 2009).
Zelmann, et al., "Improving the identification of High Frequency Oscillations," Clinical Neurophysiology, vol. 120, pp. 1457-1464 (Jul. 2009).
Kobayashi et al., "Detection of changes of high-frequency activity by statistical time-frequency analysis in epileptic spikes," Clinical Neurophysiology, vol. 120, No. 6, pp. 1070-1077 (Jun. 2009).
Brinkmann et al., "Large-scale Electrophysiology: Acquisition, Compression, Encryption, and Storage of Big Data," Journal of Neuroscience Methods, vol. 180, No. 1, pp. 185-192 (May 2009).
Bagshaw et al., "Effect of sleep stage on interictal high-frequency oscillations recorded from depth macroelectrodes in patients with focal epilepsy," Epilepsia, vol. 50, No. 4, pp. 617-628 (Apr. 2009).
Engel et al., "High-frequency oscillations: What is normal and what is not?," Epilepsia, vol. 50, No. 4, pp. 598-604 (Apr. 2009).
Jacobs et al., "Hight frequency oscillations in intracranial EEGs mark epileptogenicity rather than lesion type," Brain, vol. 132 (Pt. 4), pp. 1022-1037 (Apr. 2009).
Zijlmans et al., "High-frequency oscillations mirror disease activity in patients with epilepsy," Neurology, vol. 72, pp. 979-986 (Mar. 2009).
Final Office Action for U.S. Appl. No. 13/385,413 (dated Nov. 19, 2015).
Non-Final Office Action for U.S. Appl. No. 13/385,413 (dated May 11, 2015).
Notice of Allowance and Fee(s) Due and Applicant-Initiated Interview Summary for U.S. Appl. No. 13/385,413 (dated Mar. 15, 2016).

METHODS, SYSTEMS, AND COMPUTER READABLE MEDIA FOR VISUALIZATION OF RESECTION TARGET DURING EPILEPSY SURGERY AND FOR REAL TIME SPATIOTEMPORAL VISUALIZATION OF NEUROPHYSIOLOGIC BIOMARKERS

PRIORITY CLAIM

This application claims the benefit of U.S. Provisional Patent Application Ser. No. 61/828,173 filed May 28, 2013 and U.S. Provisional Patent Application Ser. No. 61/828,168 filed May 28, 2013; the disclosures of which are incorporated herein by reference in their entireties.

GOVERNMENT INTEREST

This invention was made with government support under grant number NS063039, RR024132, TR000139, DA022807, and NS045839 and contract number HHSN276201000492P awarded by the National Institutes of Health. The government has certain rights in the invention.

TECHNICAL FIELD

The subject matter described herein relates to systems for image guided surgery. More particularly, the subject matter described herein relates to methods, systems, and computer readable media for providing for visualization of a resection target during epilepsy surgery and for real time spatiotemporal visualization of neurophysiologic biomarkers.

BACKGROUND

Patients with drug resistant epilepsy undergo multimodal evaluation by neurologists and neurosurgeons before deciding on an appropriate treatment regimen. The multimodal evaluation may include electroencephalograph (EEG) measurements taken using a scalp electrode array, magnetic resonance imaging (MRI), and positive emission tomography (PET) imaging to identify a target region of the patient's brain for resection. The goal of these evaluations is to accurately identify the portion of the brain generating seizures so that it may be surgically resected with the goal of eliminating seizures and curing the patient of epilepsy.

Some patients undergo more invasive (Phase II) monitoring with intracranial electrodes. For such patients, intracranial electrodes are implanted in the patient. The goal is to center the intracranial electrodes over the region of the patient's brain that is causing seizures in order to capture as much information about the seizures as possible. After implantation, the patient is typically monitored for a period of two weeks to identify a resection target. The implanted electrodes are then removed and the resection target (epileptogenic focus) is removed during neurosurgery.

One problem that occurs during intracranial electrode implantation is the potential for inaccurate positioning of the electrode array with respect to the region of the brain causing seizures. In instances when noninvasive modalities are unable to provide precise information regarding the location of seizure onset, the electrode array may be placed such that only an edge of the electrode array is located over the region of the brain causing seizures. When this occurs, additional surgery may be required to reposition the electrode and repeat the Phase II monitoring.

Even when the electrode array was placed properly during Phase II monitoring, the electrode array must be removed at the time of surgical resection of the epileptogenic focus. Accordingly, the surgeon is required to remember which regions of the electrode array correspond to the regions of the brain causing the seizures without a direct reference after removal of the electrode array.

It is desirable to identify and visualize neurophysiologic biomarkers, such as those that predict or indicate seizure activity, during electrode implantation, during Phase II monitoring, and during resection surgery. However, due to growing volumes of data and the amount of processing that is required to visualize the data, systems that provide such real time visualization are not currently available. For example, raw EEG data is usually presented in two dimensional plots of detected voltage versus time. In order to be clinically useful during surgery, the occurrence of neurophysiologic biomarkers, such as high frequency oscillations, must be identified, and the occurrences must be mapped to locations of the electrodes in two dimensions or to the occurrences in an image of the patient's brain in three dimensions. With the number of electrodes in implanted electrode arrays increasing, the amount of data that must be processed has heretofore made the real time production of such an image impractical.

One particular problem that occurs during epilepsy surgery is mapping of the resection target identified preoperatively to the surgical field. Resection surgery for epilepsy is difficult because brain tissue affected by epilepsy appears visually normal. In current common practice, the preoperatively identified resection target is manually drawn on a two-dimensional cartoon of the brain for the surgeon to review interoperatively and subsequently transpose onto the surgical field. Such transposition leads to potential errors in identifying the proper resection target.

Accordingly, in light of these difficulties, there exists a need for methods, systems, and computer readable media for visualization of a resection target during epilepsy surgery and for real time spatiotemporal visualization of neurophysiologic biomarkers.

SUMMARY

The subject matter described herein relates to methods, systems, and computer readable media for visualization of a resection target during epilepsy surgery. One exemplary method includes a real time neurophysiologic biomarker visualization system implemented by at least one computer, receiving, as input, a pre-electrode-implantation MRI of an epilepsy patient's brain. The method further includes receiving, as input, a post-electrode-implantation CT scan of the patient's brain. The method further includes receiving, as input, a post-electrode-implantation MRI of the patient's brain. The method further includes receiving, as input, raw EEG data produced by an implanted electrode array and, as output, generates a visualization of occurrences of neurophysiologic biomarkers mapped to locations of the occurrences. The method further includes receiving, as input, a data identifying a resection target as defined during the extended Phase II monitoring. The method further includes receiving, as input, relative coordinates in real space produced by a neuronavigation system. The method further includes registering the MRIs, the CT scan, the visualization of the occurrence of the neurophysiologic biomarker, the data identifying the resection target, and the relative coordinates in real space produced by the neuronavigation system and outputting the registered image.

The subject matter described herein also relates to methods, systems, and computer readable media for real time spatiotemporal visualization of neurophysiologic biomarkers. According to one method, raw data collected from intracranial electrodes are received at a computational engine implemented by at least one computer. The raw data are processed to generate data indicative of occurrences of a neurophysiologic biomarker. A visualization of the processed data that maps the occurrences of the neurophysiologic biomarker and preserves their spatial configuration in either two-dimensions or in three-dimensions where at least a portion of the patient's brain corresponding to the occurrences is generated. The visualization is output to a user. The processing, generating, and outputting are performed in real-time. In one example, "real time" refers to completing the processing and visualization in a time sufficient to be useful during electrode implantation or resection surgery. The subject matter described herein may be implemented in hardware, software, firmware, or any combination thereof. As such, the terms "function" or "module" as used herein refer to hardware, software, and/or firmware for implementing the feature being described. In one exemplary implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

The subject matter described herein may be implemented in hardware, software, firmware, or any combination thereof. As such, the terms "function" or "module" as used herein refer to hardware, software, and/or firmware for implementing the feature being described. In one exemplary implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings, wherein like reference numerals represent like parts, of which:

FIGS. 2(a) and 2(b) are images of a cortical surface (white) using a marching cubes filter with an isovalue of 31. In FIG. 2(c), a 36 contact Ad-Tech electrode array implanted in a patient is shown. In FIG. 2(d), an exposed cortical tissue showing a clinically marked location of electrode contacts is illustrated. In FIGS. 2(a), (b), and (d), examples of distinct anatomical landmarks relating the surface model with the actual brain are outlined in green (or corresponding gray scale color);

DETAILED DESCRIPTION

The subject matter described herein includes methods, systems, and computer readable media for visualization of a resection target during epilepsy surgery and for real time spatiotemporal visualization of neurophysiologic biomarkers. As stated above, large volumes of EEG data output from implanted cortical electrode arrays can be difficult to interpret with conventional time-lapse displays. FIGS. 2(a), 3(a), and 4(a) illustrate examples of EEG data output from an electrode array implanted in an epilepsy patient. Although the names of the electrodes are displayed next to each EEG trace, such data is exceedingly cumbersome and almost useless during surgery or electrode implantation because multiple transpositions are required to correlate this information to corresponding locations in the patient's brain. In addition, after the electrode array is removed during resection surgery, the physician is required to remember the locations of the electrode array that detected the abnormal activity.

Figure 1:
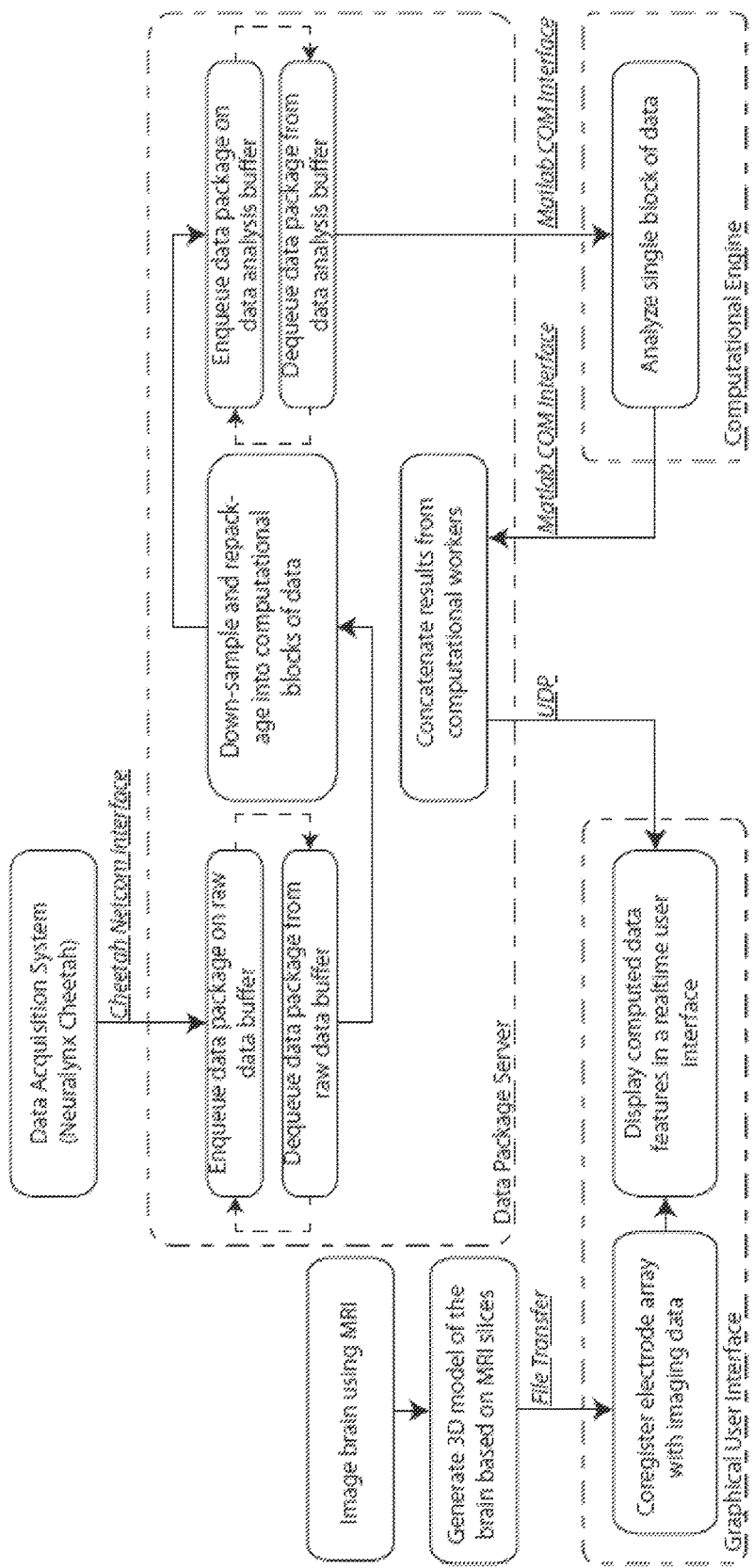
FIG. 1 is a block diagram illustrating a system for real time spatiotemporal visualization of neurophysiologic biomarkers according to an embodiment of the subject matter described herein.

In order to alleviate this difficulty, a system for real time analysis of such data to identify neurophysiologic biomarkers and provide a real time visualization of those biomarkers mapped to locations in an image of a patient's brain is provided. FIG. 1 is a block diagram illustrating an exemplary data analysis platform for real time analysis and visualization of EEG data according to an embodiment of the subject matter described herein. The system illustrated in FIG. 1 can be used for both intra- and extra-operative mapping of data derived from raw EEG data to regions of the patient's brain.

The system illustrated in FIG. 1 is capable of recording, extracting, and visualizing useful information about epileptic regions of cortex instantly allowing surgeons to optimally place the electrode array for further, more extensive, monitoring. The system illustrated in FIG. 1 is capable of processing EEG data in real time to generate data indicative of the intensity of occurrences of neurophysiologic biomarkers and to output a visualization that maps the intensities to regions of the patient's brain corresponding to occurrences of the intensities in real time. "Real time" refers to completing the processing and visualization in a time sufficient to be useful during electrode implantation or resection surgery. To enable such real time processing, in one non-limiting example, real time processing may indicate a processing time less than the data packet duration. To achieve these goals, the system illustrated in FIG. 1 includes a software package that communicates with a data acquisition system, extracts features from the recorded data using extensive parallel processing and displays these results in an interactive environment. FIG. 1 shows a schematic of the developed platform and shows how the different components interact with each other.

The platform includes three components: 1) Data Package Server, 2) Computational Engine, and 3) Graphical User Interface. External software is required to construct a 3D model of the brain based on pre-operative imaging. A high-bandwidth, multichannel data acquisition system (Atlas; Neuralynx, Bozeman MT) was used along with their proprietary interface (NetCom Development Package) to stream data in real time from the system.

The Data Package Server communicates with the data acquisition system over the NetCom interface and fetches the raw data as it becomes available. It preprocesses the data and repackages it into analytical blocks. For example, the process can downsample and repackage the raw data in 2-second non-overlapping blocks. However, sliding window implementations to create computational blocks that have overlapping data are also possible. The Data Package Server uses two rotating buffers to facilitate asynchronous preprocessing and distribution to the Computational Engine.

The Computational Engine is responsible for analyzing blocks of data and returning the results to the Data Package Server. The engine is programmed in MatLab (Mathworks, NatickMA) and interacts with the server using the MatLab COM interface. The results presented herein were generated in real-time using a single MatLab session.

Results produced by the Computational Engine are sent back to the Data Package Server which subsequently broadcasts the data via user datagram protocol (UDP). The Graphical User Interface, developed in Python using the Visualization Toolkit (VTK, Kitware Inc.), pulls results from the UDP stream and displays the spatiotemporal representation of the features in real-time. The user can specify electrode configurations, map acquisition data channels to specific electrode contacts and adjust camera zoom and viewing angle of the model during runtime.

The following sections describe three processes that cohere into the intra-operative analysis workflow: real-time EEG analysis, spatiotemporal visualization of epileptic features, and electrode co-registration.

Real-time Feature Extraction

During pre-processing the Atlas system streams EEG data over a 1.25 GBit/sec fiber optic connection to a host PC running Neuralynx's Cheetah Data Acquisition System software. Cheetah is capable of immediate downsampling, finite impulse response (FIR) filtering, signal recording and time-series display. In a second abstraction layer within this framework, we used Neuralynx's NetCom interface to connect to Cheetah's internal server over TCP/IP and stream post-processed EEG data to a local high performance PC for feature extraction.

The real-time architecture illustrated in FIG. 1 is developed in Microsoft Visual C# on the .NET Framework 4 platform and implemented on a high performance PC with 64-bit Microsoft Windows 7; Intel i7-950 CPU (8 MB cache, 3.06 GHz processing speed, four cores and eight threads) for data buffering and further pre-processing; 12 GB of RAM; NVIDIA GeForce GTX-580 (512 CUDA cores) for feature extraction. In the framework, a main engine oversees memory allocation for structuring and buffering incoming data and thread creation and destruction for three sub-processes.

The first sub-process pushes in incoming data remotely from Cheetah via NetCom. NetCom automatically handles thread creation within callback routines to accept new data asynchronously, where each data record is stored in arbitrary order in a first-in/first-out queue within the main engine. Each Neuralynx data record contains 512 samples from a single channel, a timestamp of the first sample and the sampling frequency for the whole record. Asynchronous retrieval does not ensure that channel records will be collected incrementally or chronologically. Data integrity checking and alignment are handled by a pre-feature extraction sub-process.

The main engine monitors the queue and spawns a thread to handle such processing. Each available data record is immediately downsampled in accord with the prescribed feature extraction algorithm and to relieve memory load for data buffering. This processing stage handles misaligned timestamps due to asynchronous record retrieval through linear interpolation. The data samples are chunked into feature analysis windows, filled into a feature matrix of channels x timestamp for each window, and queued into a feature extraction buffer.

Feature extraction is performed using MatLab. A COM Automation Server enables data transfer between .NET and MatLab. A feature extraction thread initiates a background instance of the MatLab COM server and sleeps until the buffer is occupied. Each feature analysis window is passed from the queue to MatLab, where user-specified, pre-tested and validated, feature extraction code returns a single feature value for each channel back to our C#-based feature server. The resulting vector represents extracted features per-channel for a single instance in time and is forwarded to the electrode mapping sub-system for visualization.

Writing feature extraction code requires efficient coding practice to reduce computational expense and minimize display latency, and consideration of system memory available for buffering data. As a general rule of thumb, the upper computational time for a particular feature analysis window cannot exceed the length of time represented by the window shift, which we call the temporal resolution of the feature analysis. High performance computing can alleviate these burdens by parallelizing feature extraction at the channel level, or algorithmic level for further efficiency. On such method of GPU-based coding using NVIDIA's CUDA language may be implemented without departing from the scope of the subject matter described herein.

High-frequency Analysis of EEG

There have been several documented studies on the utility of monitoring HFO activity for localizing epileptogenic tissue. HFOs typically consist of at least four oscillatory cycles in a spectral range of above 80 Hz. Traditional offline techniques extract HFO activity in band-passed windows of 10-minutes, where the signal root mean square (RMS) is computed with successive 3-ms sliding windows. Successive RMS values greater than 6-ms in duration and greater than five standard deviations above the mean RMS value for the entire window are considered candidate HFOs. This technique serves as a guideline to the real-time HFO visualizing algorithm presented here.

Real-time feature extraction, however, prohibits comparison of the sliding window to the entire recording. Therefore, algorithms must not only be computationally efficient, but must also be designed to function without any a priori knowledge of future signal characteristics. The HFO extraction scheme implemented by the system illustrated in FIG. 1 applies a 256-order FIR hamming window-based bandpass filter with 80 Hz and 200 Hz lower and upper cutoff frequencies in 75 ms windows with 25 ms of shift. A 25 ms temporal resolution provides visual distinction between HFO emissions across space. We then quantified HFO intensity by computing RMS in each discrete window.

Spatiotemporal Visualization of Epileptic Features

The results from the HFO analysis are presented to the user as a spatiotemporal color map on top of the 3D rendered model of the cortex. We defined a feature dynamic range (DR) as the distribution of feature values over time mapped to an 8-bit color map. Our HFO DR was generated in real-time as the running mean and standard deviation of the RMS feature output across all electrode channels. The DR ranged linearly from zero running standard deviations below the running mean to 30 above. Our DR ceiling was biased high to reduce visualization of artifactual events created by the noise floor and to capture high energy transients characteristic of HFOs. We applied a jet color map for visualizing feature intensity; however, custom color maps can also be imported.

Electrode Co-registration

Figure 2:
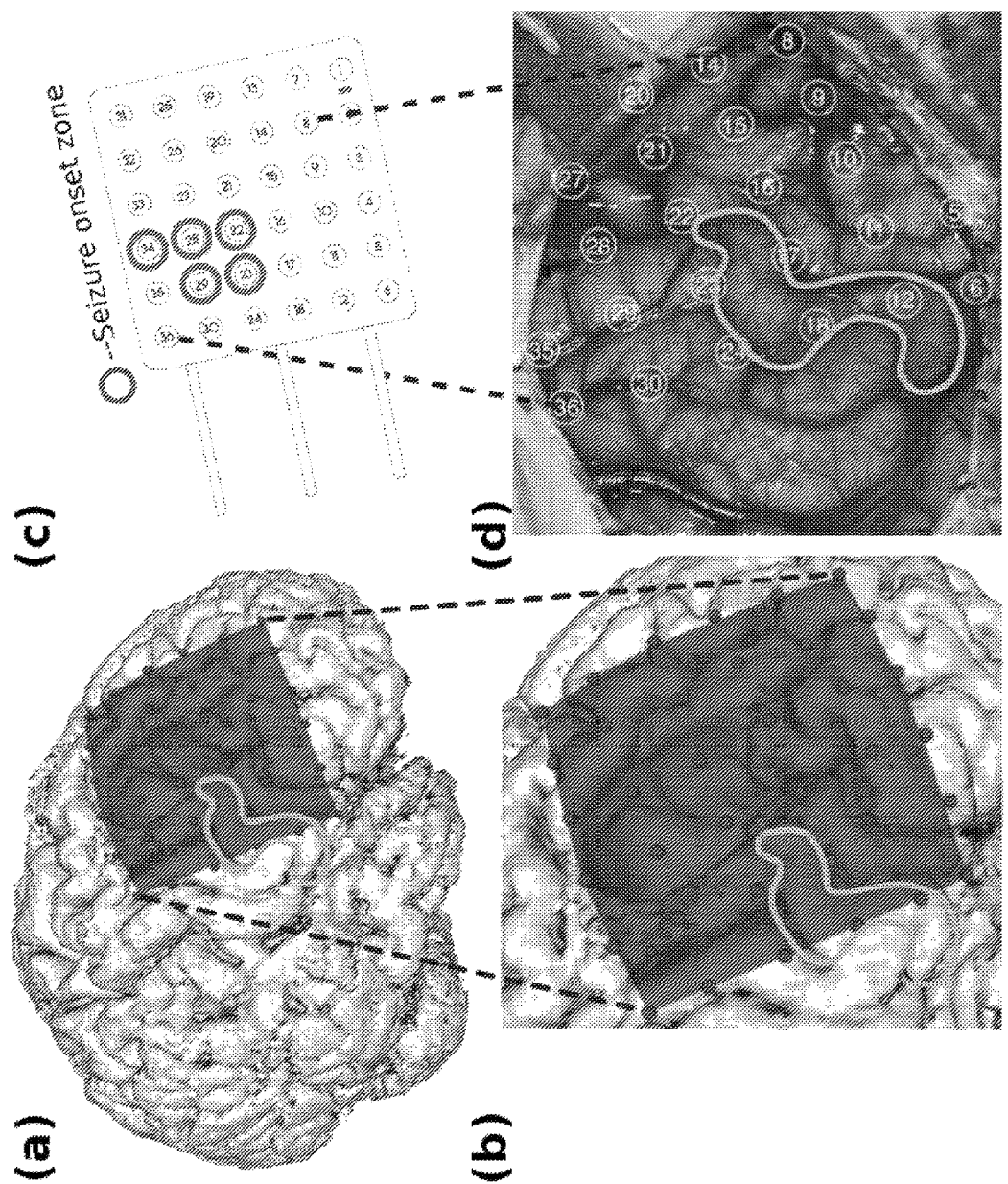
In FIG. 2, 36 visually mapped electrode contacts are represented by blue (or dark) spheres. The electrode grid surface generated by a delaunay triangulation filter is shown in red (or the dark square when shown in gray scale) revealing underlying cortical morphology.
Figure 3:
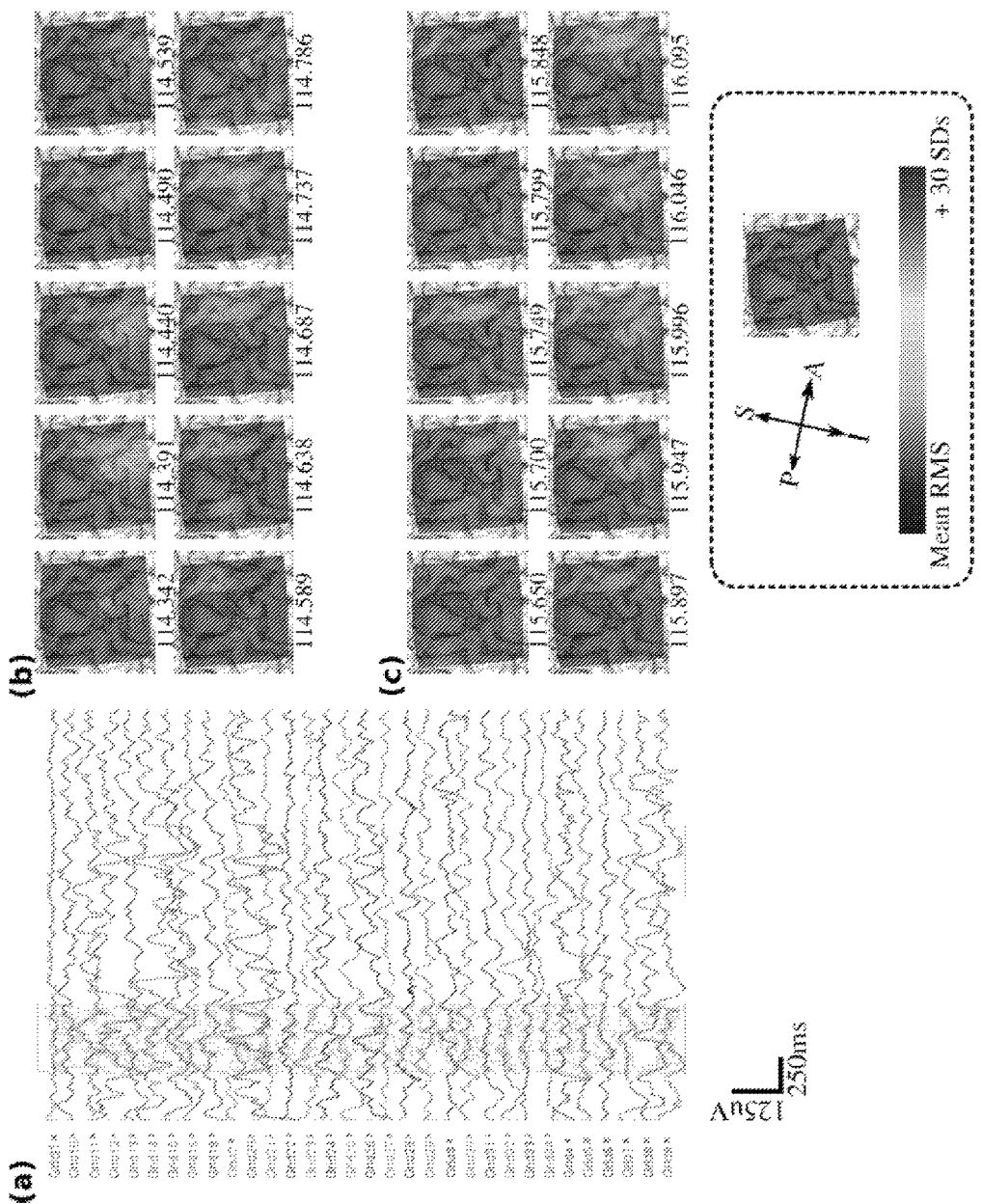
FIG. 3 illustrates interictal HFO initiation and propagation. (a) 3 seconds of EEG with two 445 ms events highlighted in red and green (or the two vertical bars in FIG. 3(a) when shown in gray scale) whose spatiotemporal structure is difficult to distinguish. (b, c) 445 ms of spatiotemporal HFO activity during the period highlighted in red (b) and green (c). Dynamics demonstrate spatial expansion and contraction of the HFO emission in the anterior region of the array outside SOZ.

The Graphical User Interface renders the 3D representation of the cortical surface using the patient's pre-operative T1-weighted MRI and the modeled representation of the electrode array, as depicted in FIG. 2. Pre-operative imaging data was used in our analysis due to availability; however, post-operative T1-weighted MRI is ideal to minimize co-registration inaccuracies. We do not expect the imaging paradigm to affect the results presented here.

The software imports MRI data from the NIfTI-1 data format. A first stage marching cubes filter based in VTK approximates a contoured surface based on tissue-specific isovalue. We deemed an isovalue of 31 to most successfully render surface-based anatomical landmarks such as sulci and gyri by comparing the render to intra-operative photographs of the cortex after craniotomy.

Using the mouse, the user could pinpoint the location of the visible electrodes on the cortical surface. Non-visible electrode locations can be extrapolated from the visible electrodes as the electrode structure is known. For the results described herein, we used the post-operative CT to verify the locations of these electrodes.

The discrete electrode contacts are then triangulated using VTK's Delaunay algorithm in order to generate a continuous, polygonal electrode surface. Although in this instance the patient was implanted with an additional strip electrode, we focused on the 6×6 grid array for the purpose of this study.

The electrode surface passes through a VTK texture mapping filter that accepts color values at polygonal nodes defined by the mapped contacts and applies linear interpolation to produce a continuous color-field. This texture mapping process is updated in real-time to reflect the spatiotemporal results of the specific feature analysis.

Proof of Concept Testing

The Atlas data acquisition system allows the user to 'playback' data to NetCom client applications. Using this feature, we mimicked extra-operative recording and real time data analysis. The following sections describe the results that were generated in real time and compare the spatiotemporal visualization to the output of a standard EEG viewer.

Platform Benchmark

A battery of tests was conducted to assess the efficiency of the developed platform. Each independent component within the framework was individually benchmarked using with a 60 second segment of data downsampled from 32,556 Hz to 2,048 Hz and recorded at 16-bit resolution.

Integrity through the Data Package Server was tested to determine dropped and misaligned records. Two confounding factors are thread management within the Data Package Server to accept incoming records and a maximum 1.0 Gbps transfer rate between Atlas and the Data Package Server. A 500 Hz, 1 mV sine wave test signal was cloned across 256 channels and recorded using Atlas. Transmission errors were measured by computing the root-mean-square error (RMSE) between the signal recorded by Atlas and the output of the Data Package Server.

Each system module's computational latency was computed using the C# StopWatch class and Python's Time module. Records consisting of 512 samples were transferred to the Data Package Server via NetCom, establishing a latency of at least 250 ms between data acquisition and visualization. Time intervals between successive NetCom callback function calls were performed to verify record receipt at 250 ms intervals. Once a particular record was received we traced the Data Package Server's latency to package samples into analytical windows for feature extraction. We tested a root-mean-square (RMS) feature extraction module in MatLab. Our visualization software pre-renders the 3D brain and electrode model to dedicate computational and graphical processing towards generating the spatiotemporal map in real-time. A single frame requires (1) updating the feature dynamic range, (2) mapping the feature to a color, and (3) interpolating and rendering the electrode surface with the new feature colors. We measured the average time to draw a single frame to the screen.

The results of our benchmarks are presented in Table 1. The RMS error was minimal across 256 channels and we expect channel reduction or a decrease of sampling frequency to result in less dropped packets. We estimated a total input to visualization latency of approximately 20.7 ms. We emphasize that the feature extraction complexity largely guides this latency and will affect the analytical window size to satisfy the 'real time' constraint.

TABLE 1

Platform benchmarks verifying integrity of data transmission and latency of data retrieval, packaging, feature extraction and display

| Pipeline | Description | Measurement |
| --- | --- | --- |
| Data Integrity | Root-mean-square error | 11.647 µV |
| NetCom Callback | Latency between records | 0.972 ± 15.2 ms |
| Data Package Server | Latency to analytical window | 0.171 ± 0.462 ms |
| MATLAB Feature Extraction | Root-mean-square calculation time | 2.2 ± 2.4 ms |
| 3D Render and Visualization | Latency of single frame draw | 17.4 ± 6.4 ms |

Post-operative Patient Study

The subject whose data was analyzed in this study was a woman who presented with recurrent epilepsy 3 years after having an oligodendroglioma surgically resected at another institution. She had simple partial seizures that began with an aura, followed by turning of her head to her left with left-sided face and extremity twitching. As part of her initial evaluation, she underwent an MRI, which demonstrated a residual or recurrent tumor posterior to the resection cavity. While scalp EEG captured two seizures originating from the right frontal lobe, interictal single-photon emission computed tomography (SPECT) was able to confine the SOZ to the posterior aspect of the frontal cortex, just behind and below the surgical cavity. Given the need to better define the relationship between the tumor and the SOZ, the patient underwent invasive intracranial monitoring. An 8-contact subdural strip electrode was placed over the motor cortex, immediately behind a 66 subdural grid electrode array in order to cover the aforementioned region of interest. Tufts of 40 micron diameter microelectrode contacts were embedded in the grid and adjacent subdural strip electrode, fabricated by AdTech Medical (Racine, Wis.). Twelve seizures captured during the patient's intracranial in-patient monitoring phase demonstrated focal runs of 5 Hz spike-wave complexes that started posterior to the resection cavity in the area of the residual tumor and spread upwards, over the convexity of the frontal lobe. Stimulation tests performed with the implanted electrodes were used to help confirm the SOZ and define its relative location to the primary motor cortex and speech areas. With a consensus between these multiple diagnostic modalities, the patient was taken to the operating room for removal of her hardware and resection of the residual tumor and surrounding SOZ. Once again, pathology was consistent with a Grade 2 oligodendroglioma. The patient's post-operative MRI demonstrated complete resection of the tumor and she was initially seizure-free. Unfortunately, she suffered a recurrence of her seizures approximately 14 months after her surgery.

Cortex Visualization and Electrode Placement

We focused on a single 6×6 electrode array that was implanted subdurally over the right frontal lobe, centered over the suspected SOZ along the posterior margin of the resection cavity. FIGS. 2(a) and (b) show the model of the cortex with the modeled electrode array overlaid. Clearly identifiable cortical structures are outlined in FIGS. 2(a), (b), and (c).

Interictal Visualization

In most patients epileptic brain usually exists in an interictal (between seizure) state, where normal functioning continues, sometimes in parallel to sub-clinical ictal (seizure) events that occur unknown to the patient, resembling seizure morphology or abnormal discontinuity in EEG.

During the post-operative monitoring phase, we visualized the spatiotemporal profile of HFO activity in real-time during these states and found fast events of short HFO activity in localized portions of the electrode grid. During three seconds of EEG recorded 15 seconds prior to seizure onset, two examples of interictal HFOs are detected despite the lack of any obvious trends related to epileptic activity are shown in FIG. 3(a). On a millisecond scale, we observed simple patterns of HFO activity located outside the SOZ (FIGS. 3(b) and (c)). Specifically, we recognized focal regions of high-energy HFOs surrounded by adjacent regions of attenuated HFO activity. These events typically spread along a neighborhood of five electrode contacts covering 60 mm2 of cortical tissue and lasting less than 500 ms.

Preictal Visualization

The ten seconds preceding the seizure was characterized as the preictal state, for the purpose of the present study. We present four seconds of EEG activity during this state beginning seven seconds prior to seizure onset in FIG. 4. During this period we observed sustained HFO activity for 3.7 seconds in the SOZ (FIG. 4(b)); while temporal structure in the time-series (FIG. 4(a)) at conventional gain and time scale did not indicate SOZ-related high-energy activity. The dynamics of the event is represented by a transient rise in energy in the "HFO zone" (122.121 seconds), local propagation 200 ms later, and a contraction back to the origin at the end of the event (125.875 seconds). HFO energy was focal, coinciding with three electrode contacts together covering 36 mm2 of cortical tissue. Spatial discrimination of the event was facilitated by a strong attenuation of HFO energy outside the SOZ.

Ictal Visualization

Figure 5:
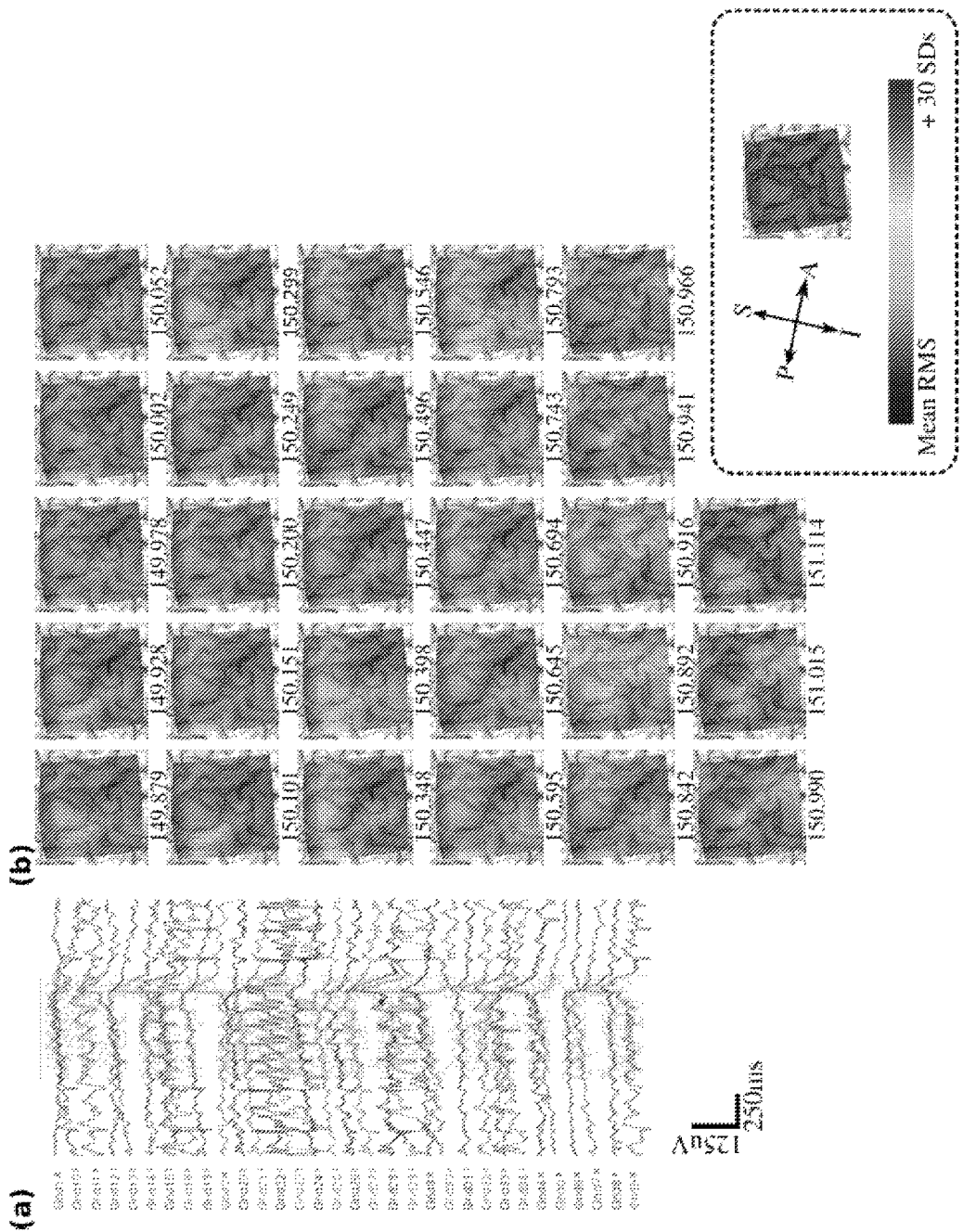
FIG. 5 illustrates ictal HFO initiation and propagation. (a) 3 seconds of EEG of 25 second long seizure with event in red (see vertical bar in FIG. 5(a)) distinguishing heavy spiking leading to large final spike 3.2 seconds prior to seizure suppression. (b) high energy HFO activity spread across array with transient activation in the clinically-determined SOZ. HFO activity coinciding with seizure suppression is evident outsize SOZ on the anterior inferior margin of the array.

Seizure duration was 25 seconds characterized by bursts of spike activity from distinct channels within the SOZ leading to a strong single spike on numerous channels 3.2 seconds prior to the seizure's end and background suppression, observed on the conventional EEG time trace (three seconds shown in FIG. 5(a)). HFO energy was spatiotemporally diffuse during the ictal period (FIG. 5(b)). Despite a general rise in energy across the area of the grid, transient rises of HFO "hotspots" were focal to the SOZ (150.447 seconds to 150.743 seconds). Small HFO hotspots were occasionally observed outside of the SOZ (150.151 seconds, 150.595 seconds) and were brief. The spatial origin of the final spike event in the seizure (150.892 seconds) was unremarkable at this temporal resolution. However, the post-event images made apparent two regions of high HFO energy (150.941 seconds to 151.015 seconds) and spatial retraction of HFO energy back to the SOZ was finally evident (151.114 seconds).

Discussion

The subject matter described herein addresses the need for intra-operative access to real-time analysis of subdural EEG in order to accurately place electrode arrays for long-term monitoring in patients with refractory epilepsy. Currently, electrode placement is guided by pre-operative scalp EEG screening in combination with MRI imaging. However, inconsistent placement and inaccuracy can result in inadequate positioning of the array and failure to locate the epileptic focus during subsequent monitoring sessions. A discussion about the possibilities of intra-operative, real-time analysis of intracranial EEG is provided below. In addition, we discuss the advantages of visualizing features in a spatiotemporal map of discrete EEG biomarkers versus standard EEG time traces. Lastly, we present future applications of co-registration of the spatiotemporal map and the patients MRI for purposes of streamlined surgical resections.

Real-time Data Analysis Platform

Technological advances drive the feasibility of analysis of complex features in a real-time environment. Above we demonstrate that these technologies provide additional useful information that is not observable with current EEG monitoring systems. We expect that these augmented visualization techniques may emerge as standard techniques for real-time evaluation of cortical activity, at least to compliment more traditional EEG time tracings.

Intra-operative monitoring of complex features in multi-channel EEG is a natural extension of the techniques we present. This could provide a useful tool for finding the optimal location for subdural electrode array placement, based upon HFO detection and recording, prior to in-patient intracranial monitoring and consequent functional brain mapping and resection of a patient's epileptic network. Using real-time analysis of cortical feature density, surgeons would be able ensure adequate coverage of the area of interest, while avoiding implantation over areas of uninvolved cortex. This improvement not only helps to decrease the time required for electrode mapping in a fast-paced intraoperative environment, but also may reduce the volume of hardware that has to be implanted. It is important to note, should this technique be used, that intraoperative sampling be guided by appropriate statistical measures to distinguish HFO-generating areas from background HFO activity emanating from normal brain regions.

Intra-operative Analysis of Cortical Activity

Recent findings of interictal HFO activity correlating with the SOZ suggest that long term monitoring might ultimately be unnecessary, should these results be borne out in randomized, controlled clinical trials. The ultimate goal would be to evaluate epileptic activity intra-operatively, define the SOZ, and perform the resection in a single operation. The results from this retrospective patient case study demonstrate the usefulness of mapping HFO activity for localization of the seizure onset zone and adjacent regions which might constitute a patient's epileptic network.

Of interest, we found sustained increases in the HFO energy-bands (80-200 Hz) that occur preictally within the SOZ, while interictal HFO energy was localized primarily outside of the SOZ, and displayed vastly different spatiotemporal structure. These findings suggest that different underlying cortical mechanisms may give rise to these unsustained and more diffuse events. Since ictal HFO energy was spread throughout the electrode array, localization of hot spots was difficult; however, only the SOZ was characterized by unsustained rises in HFO energy during the ictal phase. Although these findings might be considered preliminary, they exemplify the possibilities of these technologies. It will be important to validate these findings in larger, controlled studies in larger numbers of patients.

When using intra-operative measures of cortical activity for grid placement, one must bear in mind that anesthesia can suppress cortical activity related to seizure generation, however, found that intra-operative interictal spike frequency correlates well with visually marked seizure onset zone in children. Since the data analyzed for our study was recorded post-operatively, results may be attenuated when performing the same analysis intra-operatively. Ultimately, our data provide an excellent starting point for a fruitful collaboration between the surgical team and researchers involved with this study. We expect to utilize these tools intra-operatively in the near future. With a focus on intra-operative implantations, the specific HFO algorithm that was implemented for the analysis of this data was written to be fast and exemplary for this study. We acknowledge that other algorithms might provide more accurate and specific results but would also add a computational cost. For example, found that the fast ripple band (250-500 Hz) correlates better with the SOZ. While significantly more investigation into the clinical significance of HFOs and optimal algorithm for feature analysis is necessary, these topics are beyond the scope of this study. Regardless of the algorithm used for feature extraction, the modularity of the presented framework allows for the implementation of demanding computational analysis, as well as utilization of the graphics processing unit (GPU).

Co-registration of Spatiotemporal Maps with Cortical Images

Accurate co-registration of the grid with the cortical surface model of patient brain adds to the utility of this technology. The subject matter described herein includes a method of individual contact-based point clicking for mapping electrode location in the virtual environment. Currently, we are exploring more elegant solutions using virtual electrode models that conform to the rendered brain surface, which can be rotated, translated and registered with a single-click. Techniques for projecting intra-operative photographs of the craniotomy onto the computer-generated virtual models can be adapted to localize the virtual-representation of the electrode grid. Such an approach can reduce the burden of manually transposing electrode locations from the real environment to the virtual environment.

A spatiotemporal heat map superimposed onto a post-implantation MRI or CT will help streamline both monitoring phase and surgical resection itself. In both instances, electrode reference numbers could remain internal to the system, allowing clinicians to converse in a language based solely on anatomic location eliminating transposition of information and reducing the likelihood of medical errors. During the monitoring phase, knowledge of specific electrode locations will aid clinicians in optimally correlating patient behavior, symptoms, brain regions and EEG for better therapeutic outcome. In addition, the modular nature of this system would allow clinicians to select one or more feature extraction algorithms to help accurately define the SOZ. Once defined, the SOZ may be highlighted on the cortical image, which could be utilized directly by current intra-operative image-guided navigation systems. Such an implementation would allow surgeons to define the SOZ intra-operatively without the need for the additional step of transposing electrode reference numbers. As such, anatomical landmark data coinciding with a 3D virtual representation of the patient brain will add to existing methodology of EEG monitoring, functional mapping, and stimulation to help surgeons with planning resective surgery.

CONCLUSION

The subject matter described herein includes a software platform that can be used to analyze and visualize spatiotemporal data features in real-time, intra- and extra-operatively. We demonstrate that the spatiotemporal feature map provides meaningful information in a more intuitive interface that presents information and selected signal characteristics in a more apparent manner than traditional time-traces. We believe that having access to such information intra-operatively can aid the surgical team to optimally place subdural electrode arrays. Furthermore, integration with current imaging technologies will help to streamline the processes of SOZ delineation, surgical resection, and hopefully improved patient outcome.

Figure 6:
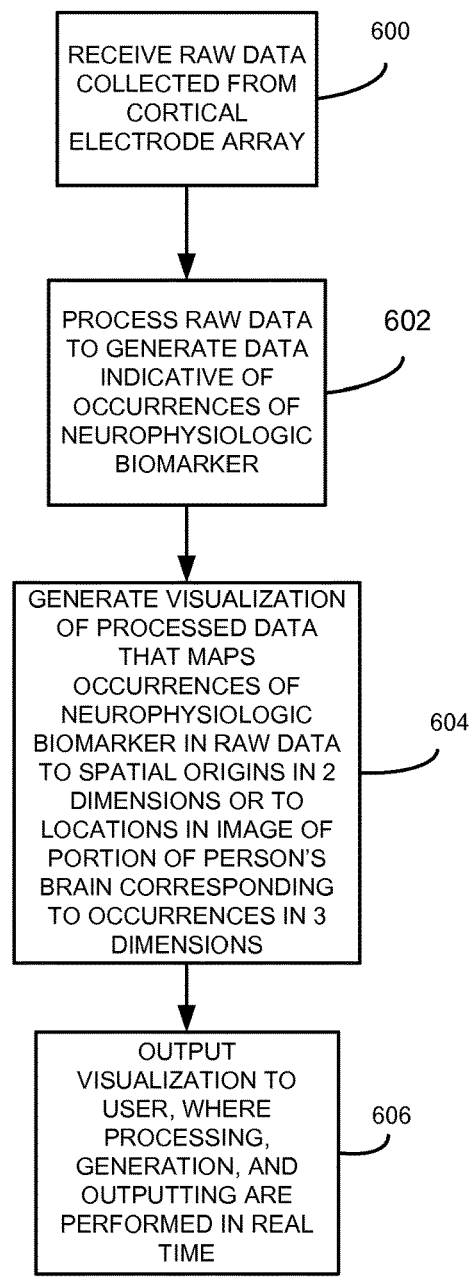
FIG. 6 is a flow chart illustrating an exemplary process for real time visualization of data that maps occurrences of a neurophysiologic biomarker to locations in an image of a portion of a patient's brain according to an embodiment of the subject matter described herein.

FIG. 6 is a flow chart illustrating a process for real time visualization of neurophysiologic biomarkers according to an embodiment of the subject matter described herein. Referring to FIG. 6, in step 600, the method includes receiving, at a computational engine implemented by at least one computer, raw data collected from a cortical electrode array. For example, as illustrated in FIG. 1, the computational engine receives raw data from a cortical electrode array. In step 602, the method further includes processing the raw data to generate data indicative of occurrences of a neurophysiologic biomarker. For example, the computational engine illustrated in FIG. 1 may process the raw data to detect HFOs, using the methods described above. Alternatively, to extract a different neurophysiologic biomarker, a plugin specific to that biomarker may be defined, and the plugin may be used to configure the computational engine to identify occurrences of that biomarker in the raw data. In step 604, the method further includes generating a visualization of the processed data that maps the occurrences of the neurophysiologic biomarker to its spatial origins in two-dimensions or to locations in an image of at least a portion of a patient's brain corresponding to the occurrences in three dimensions. In step 606, the method includes outputting the visualization to a user, wherein the processing, generating, and outputting are performed in real time.

Figure 7A:
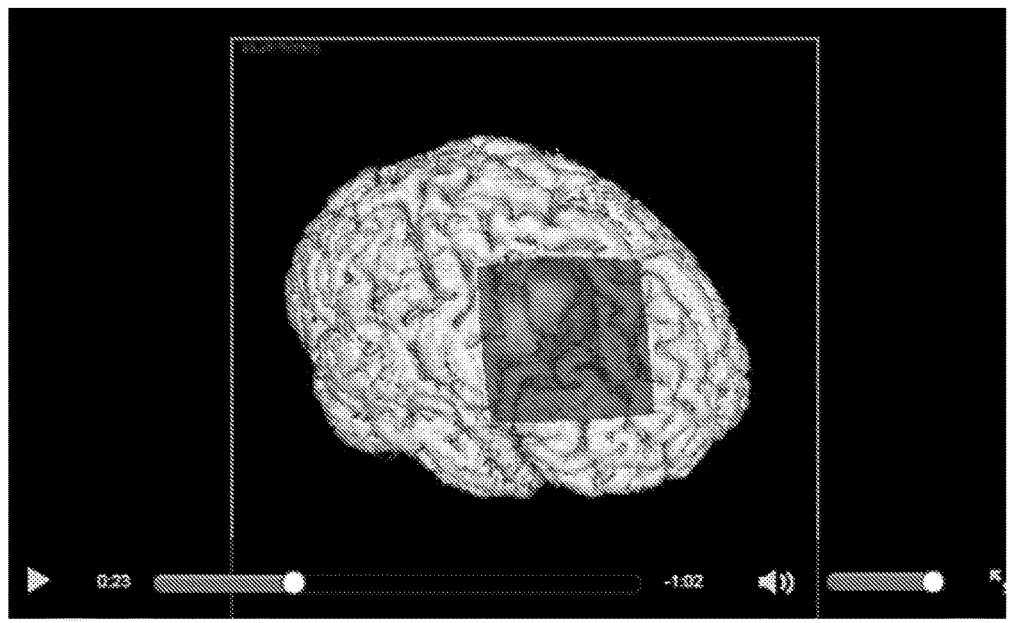
FIGS. 7(a) and 7(b) are images of heat maps that indicate occurrences of a neurophysiologic biomarker mapped to regions in an image of a person's brain according to an embodiment of the subject matter described herein.
Figure 7B:
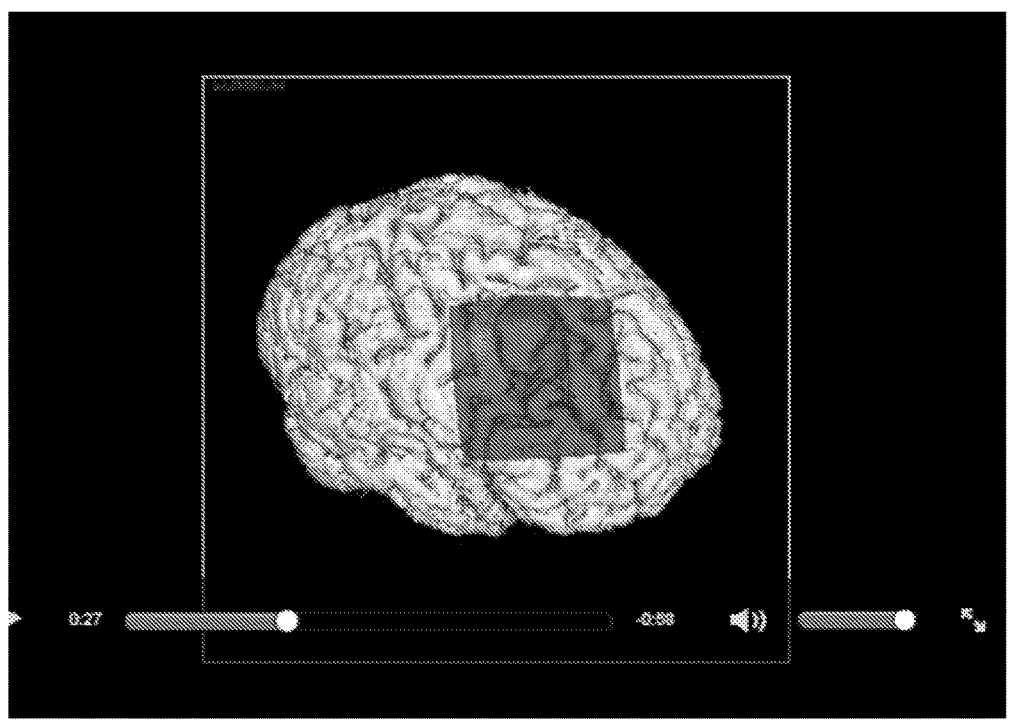

FIGS. 7(*a*) and 7(*b*) illustrate examples of visualizations that may be output and updated in real time using the subject matter described herein. In FIG. 7(*a*), the brain image was derived from pre-implantation MRI data, post-implantation MRI data, and post-implantation CT data, as described above. The gray square is an image of the electrode array, which may be manually or automatically registered with the brain image. The electrode array is shown in partial transparency so that activity corresponding to HFOs can be visualized. Such activity is shown by the yellow and green (or corresponding gray scale) colors beneath the electrode array. As the occurrences of the neurophysiologic biomarker change with location and time, the system automatically updates the visualization in real time, as illustrated by the differences in color of the heat map between FIGS. 7(*a*) and 7(*b*).

Also, the subject matter described herein is not limited to mapping occurrences of the neurophysiologic biomarker to locations of the occurrences in an image of the patient's brain in 3D, as illustrated in FIGS. 7(*a*) and (7*b*). In an alternate implementation, as set forth above, occurrences of the neurophysiologic biomarker may be mapped to locations on the implanted electrode that detected the occurrences in 2D. Thus, an alternate visualization that may be produced by the subject matter described herein is a two dimensional visualization of the electrodes with a heat map of occurrences of the neurophysiologic biomarker mapped to the 2D rendering of the electrode array.

Intraoperative Tool for Visualization of Resection Target during Epilepsy Surgery As set forth above, the subject matter described herein may be used to provide an intraoperative tool for visualization of a resection target during epilepsy surgery. The system will assist neurosurgeons by leveraging computational image guidance to clearly visualize a resection target as it was defined preoperatively. In order to accomplish this task, the system may superimpose the user-defined area or volume based on preoperative neurophysiologic recordings onto a 3D reconstruction of the patient's brain. The maps will be superimposed onto an image set composed of co-registered MRI and CT scan data obtained after subdural electrode implantation. The co-registration process eliminates human error in determining the locations of electrodes on the cortical surface. This technology allows physician defined areas of seizure generation to be directly visualized with respect to cortical surface landmarks. The system will provide an intuitive graphical user interface that allows physicians to define the target for surgically resection by simply selecting the electrode contact of interest. The system will use this information to highlight the selected contacts on the registered image set, thereby defining the resection target on the cortical surface, which can be used for intraoperative guidance.

According to one aspect, it will be possible to the load the generated image set onto a neuronavigation system for utilization during epilepsy surgery. Rather than manually transposing the predetermined resection target from the 2D cartoon during the procedure, the proposed system will provide an area over the cortical surface that can be visualized on the navigation system and related to real space with a standard navigation pointer. Although many surgeons currently utilize image guidance during surgical resections, current technology does not directly provide information regarding the defined resection target as characterized by long term EEG data.

Figure 8:
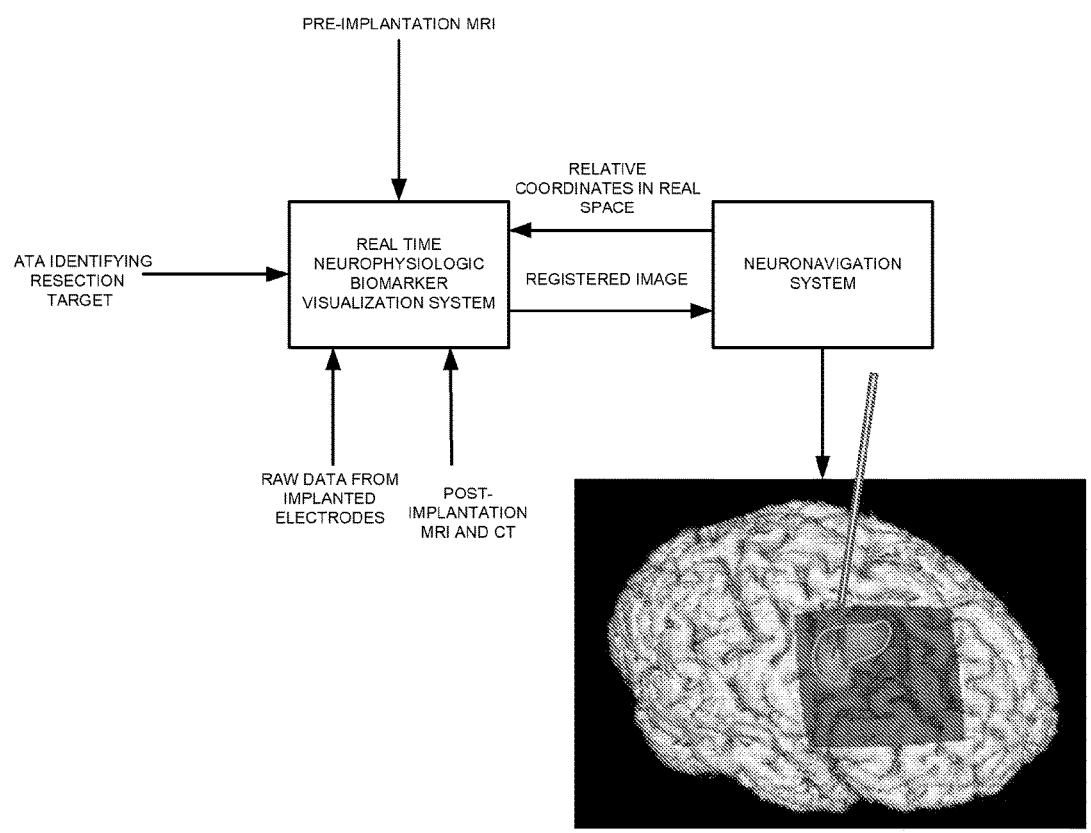
FIG. 8 is a block diagram illustrating a system for visualization of a resection target during epilepsy surgery according to an embodiment of the subject matter described herein.

FIG. 8 is a block diagram illustrating an exemplary system for visualization of a resection target during epilepsy surgery according to an embodiment of the subject matter described herein. Referring to FIG. 8, a real time neurophysiologic biomarker visualization system, such as that illustrated in FIG. 1, receives as inputs, a pre-implantation MRI, raw data from implanted electrodes, post-implantation MRI and CT data. This data may be used to generate images, such as those illustrated in FIGS. 7(a) and 7(b) that display a heat map that identifies the occurrences of a neurophysiologic biomarker mapped to regions of the patient's brain. The real time neurophysiologic biomarker visualization system may also receive as input data identifying a resection target. For example, a physician may define an area or region that surrounds the areas of neurophysiologic biomarker occurrences in the heat map. The physician may input this data by selecting the regions of biomarker occurrences using a graphical user interface. The real time neurophysiologic biomarker visualization system may receive input from a neuronavigation system of relative coordinates in real space collected by the system during surgery. For example, the neuronavigation system may include one or more cameras, such as infrared cameras, that track objects and landmarks on the patient during surgery. The locations of the tracked objects, such as surgical tools or pointers, and the landmarks may be provided to the real time neurophysiologic biomarker visualization system. In conjunction with the neuronavigation system, the real time neurophysiologic biomarker visualization system may output an image of the resection target registered with an image of the patient's brain. The result may be similar to that illustrated in FIG. 8 where the image includes an image of the patient's brain, a green (or corresponding gray scale color) area that defines the resection target, an image of a tracked object, such as a tool used in resection surgery and the heat map illustrating occurrences of the neurophysiologic biomarker. The tracked object in FIG. 8 is the elongate object that extends inside the resection target area identified by the closed area that represents the resection target.

Figure 9:
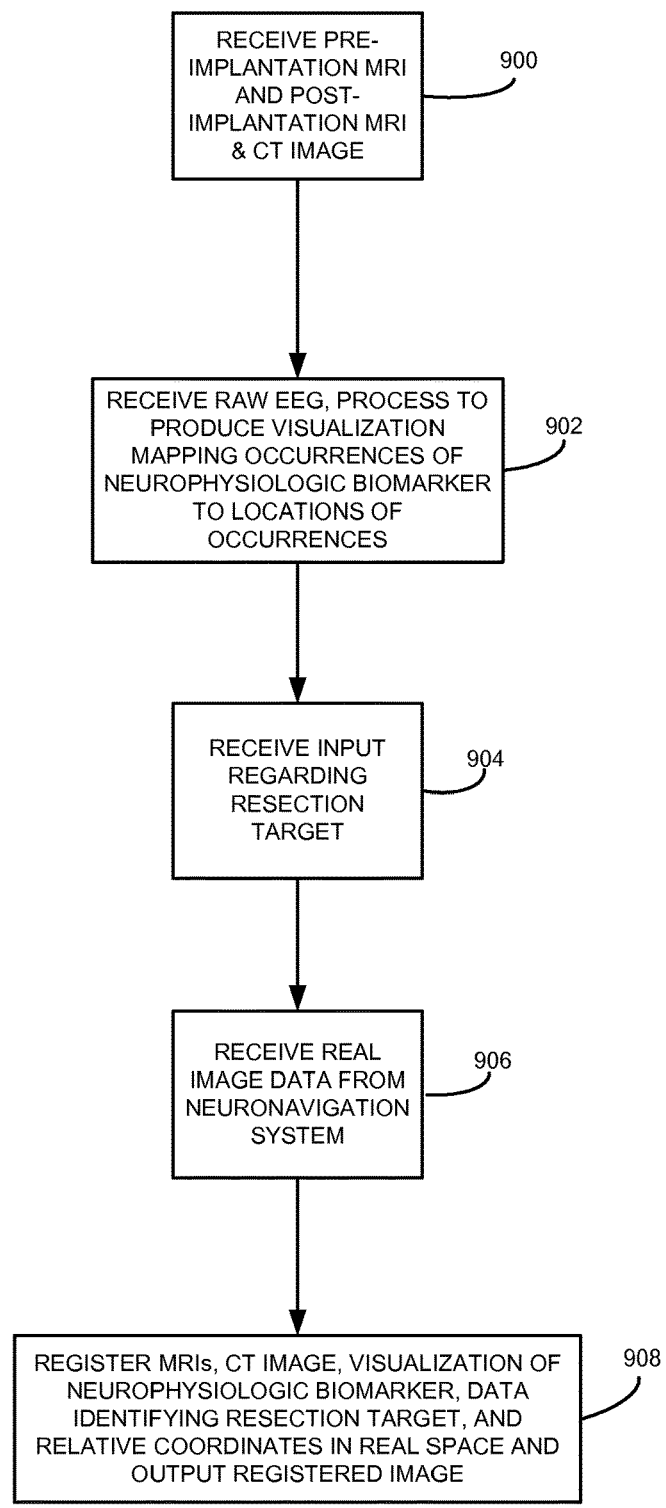
FIG. 9 is a flow chart illustrating an exemplary process for visualization of a resection target during epilepsy surgery according to an embodiment of the subject matter described herein.

FIG. 9 is a flow chart illustrating an exemplary process for providing an intraoperative tool for identification of a resection target during epilepsy surgery. Referring to FIG. 9, in step 900, a real time neurophysiologic biomarker visualization system receives as input a pre-electrode-implantation MRI, a post-electrode implantation CT image, and a post-electrode implantation MRI. For example, the pre-implantation MRI may be a high resolution MRI, such as a 3.0 Tesla MRI. The post-implantation MRI may be a lower resolution MRI, such as a 1.5 Tesla MRI.

In step 902, the visualization system receives as input raw EEG data collected from implanted electrodes and produces a visualization of occurrences of a neurophysiologic biomarker mapped to locations of the occurrences. For example, the system illustrated in FIG. 1 may receive raw EEG data and produce a heat map of occurrences of HFOs or other neurophysiologic biomarkers using the methods described above.

In step 904, the system receives as input data indicative of a resection target. For example, the system illustrated in FIG. 1 may receive input from a user, such as a neurosurgeon, via a graphical user interface, that bounds or defines a region in an image of the patient's brain corresponding to a resection target. In one embodiment, the user may use a graphical pointer or other tool to bound an area or region indicating high occurrences of the neurophysiologic biomarker as output on the heat map. An example of such a region is illustrated by the green (or corresponding gray scale) shape mapped to the image of the patient's brain in FIG. 8.

In step 906, the system receives as input relative coordinates in real space produced by a neuronavigation system. For example, the neuronavigation system may include one or more cameras that track landmarks positioned on the patient and instruments used by the surgeon. The relative coordinates in real space may indicate the locations in an image space of the neuronavigation system of the tracked objects and the landmarks.

In step 908, the system registers the MRIs, the CT image, the visualization of occurrences of the neurophysiologic biomarker, the data identifying the resection target and the relative coordinates in real space and outputs a registered image. For example, the real time neurophysiologic biomarker visualization system may output an image similar to that illustrated in FIG. 8 that includes an image of the patient's brain, a visualization of occurrences of the neurophysiologic biomarker indicated by the heat map, a visualization of the data identifying the resection target, identified by the green (or corresponding gray scale) shape drawn around the high intensity portions of the heat map, and the visualization of relative coordinates in real space from the neuronavigation system, indicated by the instrument shown in red. Registering the images, the visualization, and the data may include mapping all of the separate inputs to a common coordinate system. The combined image may be output via the normal output display system of the neuronavigation system to facilitate resection surgery. The image may be continually updated as the locations of tracked objects changed and the locations of occurrences of the neurophysiologic biomarker change.

The subject matter described herein is not limited to the ordering of steps illustrated in FIG. 9. For example, the inputs may be simultaneously received or nearly simultaneously received by the real time biomarker visualization system without departing from the scope of the subject matter described herein.

The disclosure of each of the references listed in PCT Application No. PCT/US2014/039865 is hereby incorporated herein by reference in its entirety.

The following describes a fully automated pipeline for visualization of subdural electrodes using 3D CT-MRI co-registration according to an embodiment of the subject matter described herein.

Summary

Purpose: Visualization of subdural electrodes in 3D space can greatly aid in surgical planning for epilepsy patients. Given that prior practices of manually drawing electrodes onto 2D cartoon images of the brain is inaccurate and prone to human error, several new software algorithms that co-register CT and MR images have been created to improve electrode visualization. Many of these methods are still in their infancy, have yet to be rigorously validated, and are not standardized across epilepsy centers. The few software algorithms that can be purchased are only available at an exorbitant cost. The more accurate 3D electrode visualization algorithms rely on intra-operative photographs, but these techniques are operator-dependent and electrodes under the skull cannot be visualized. Using a fully automated open-source algorithm, we have developed and tested a novel method for accurate 3D visualization of all electrodes using post-implant CT and post-implant MR images. Methods: CT-MR rigid brain co-registration, MR non-rigid brain registration, and prior-based brain segmentation were carried out on 7 subjects. The post-implant CT, post-implant MR, and an external labeled atlas were then normalized to the same space. Validation of the co-registration algorithm was performed by manually marking identical anatomical landmarks on the post-implant CT and post-implant MR images. Following co-registration, the distances between the center of the landmark masks on the post-implant MR and the co-registered CT images were calculated for all subjects. Key Findings: Brain image registration and segmentation was successfully performed on all subjects. Despite post-operative brain deformation, the proposed pipeline was able to automatically align intra-subject multi-modal images and segment cortical subregions such that all electrodes could be visualized on the parcellated brain. Manual marking of anatomical landmarks validated that the co-registration was accurate, with a mean misalignment distance of 2.87±0.58 mm between the landmarks.

Significance: We have demonstrated accurate 3D visualization of all subdural electrodes on a parcellated brain. Our method of 3D electrode visualization is one of the most rigorously validated for all subjects using quantitative measures. This pipeline is unique by involving no pre-processing, being fully automated, and the first of its kind to be freely available worldwide. It is accessible as an open-source platform on the International Epilepsy Electrophysiology Portal (https://www.ieeg.org/).

1. Introduction

Surgery is the most effective treatment for intractable drug-resistant partial epilepsy (Wiebe et al., 2001; Engel et al., 2003). In the presurgical evaluation, scalp EEG and non-invasive techniques are limited in determining the precise location of the ictal onset zone, necessitating the need for implantation of subdural electrodes for electrocorticography (ECoG). Such invasive monitoring is used for more precise localization of the ictal onset zone and seizure spread, as well as enabling cortical stimulation mapping. ECoG findings are outlined with respect to electrode locations, with accuracy of the subsequent resection target regions being dependent on clear and exact visualization of this combined electrode map relative to the cortical surface. Increasingly across many epilepsy centers, pre-operative imaging tools are being employed for 3D electrode visualization on a reconstructed post-implantation brain image. Beyond translation of ECoG results with respect to precise localization on a 3D image, these more accurate electrode visualization tools can help improve the integration of intracranial electrophysiological data with other imaging modalities that map the epileptic network, identify eloquent cortical regions, and provide functional localization data obtained from fMRI and MEG recordings overlaid on pre-surgical MRI scans (Pieters et al., 2013).

To date many different imaging techniques have been employed for visualization of intracranial electrodes. Such methods include projecting lateral skull radiographs onto MRI (Winkler et al., 2000), curvilinear reformatting of 3D MRI (Shulze-Bonhage et al., 2002), surface CT reconstruction (Hunter et al., 2005), and fusing intraoperative digital photography with pre-implantation MRI (Wellmer et al., 2002; Dalal et al., 2008). Recent labor intensive methods have been developed that rely heavily on intraoperative photographs and avoid conventional techniques of CT-MRI co-registration (Pieters et al., 2013). These techniques have been validated more rigorously than earlier work outlined above, with electrode localization error results that are very promising. These methods that rely on intraoperative photographs have limitations given that not all electrodes can be visualized on the final 3D rendered image. MRI matching to photographs primarily relies on electrodes that are in view of the camera. Given that electrodes are often positioned under the skull and away from the exposed cortex, electrode contacts on the outer boundaries of the grid as well as strip electrodes may not be visualized (Hermes et al., 2010).

Although not as rigorously validated and with higher electrode localization error, many epilepsy centers use more commonly practiced methods of conventional post-implant CT and pre-implant MRI co-registration to generate a final 3D image showing a display of the implanted electrodes relative to cortical anatomy (Immonen et al., 2003; Ken et al., 2007; Morris et al., 2004; Nelles et al., 2004; Sebastiano et al., 2006; Silberbusch et al., 1998; Tao et al., 2009). These algorithms employ surface oriented, mutual-information based, or landmark-based methods (Nelles et al., 2004). Limitations are error-prone pre-processing (e.g. brain surface extraction, skull segmentation) and manual specification of landmarks used for co-registration. Most of these algorithms also rely heavily on projection of the electrodes onto the cortical surface. Such is the case due to brain shift that occurs during and after subdural electrode implantation. This is due to thickness of the implanted material, as well as blood and fluid accumulation underneath the craniotomy flap used for subdural electrode implantation (Studholme et al., 2001; Skrinjar et al., 2002; Elias et al. 2007; Hastreiter et al., 2004). This nonlinear deformation especially affects electrodes under the bone flap, causing them to be buried when visualized in a model created by the pre-implant MRI (Pieters et al., 2013; Hermes et al., 2010). This effect is minimized when the post-implant CT is co-registered to the post-implant MRI, minimizing the effect of brain shift on the final 3D rendered image.

The aim of this study is to demonstrate the feasibility of a novel method of CT-MRI co-registration that allows for accurate and reliable 3D visualization of all electrodes by co-registering the post-implant CT with the post-implant MRI. The final image showing the electrodes is displayed on a parcellated brain with rich cortical annotation. In conjunction with results of cortical stimulation mapping, the goal of the parcellated brain image is to aid in determining the boundaries of target regions for surgical resection. Our proposed method is also fully automated and takes advantage of leading techniques in the field of brain registration and segmentation. We are able to visualize all electrodes contacts and minimize the effect of brain shift on electrode visualization by co-registering the post-implant CT with the post-implant MR image. This method is one of the most rigorously validated CT-MRI co-registration algorithms for visualization of intracranial electrodes, and is among the first to be done on a parcellated brain. We are also the first group to establish our algorithm as an open-source platform on the International Epilepsy Electrophysiology Portal (https://www.ieeg.org).

2. Methods 2.1 Patients and Electrodes

Seven patients with intractable drug-resistant epilepsy were included in the experiments to test the efficacy of the proposed automated electrode visualization pipeline. All subjects underwent implantation of subdural electrodes for intracranial EEG monitoring. Mean age at implantation was 31 years (range 21-42). Four of the subjects were male and three were female. This study was approved by the Institutional Review Board of the University of Pennsylvania.

The placement of electrodes was individualized based on findings of presurgical evaluation.

Platinum electrodes embedded in a silastic membrane (Ad-Tech Medical Instrument Corporation, Racine, Wis.) were used. The diameter of the electrode disc was 5 mm and electrode spacing from center to center was 10 mm. The implanted units had between 4 and 64 contacts (grids: 8×8, 4×8, 2×8, strips: 1×4, 1×6, 1×8). The electrodes were implanted on the frontal, temporal, and parietal regions (right hemisphere in two subjects, left hemisphere in two subjects, bilaterally in three subjects). Six subjects were implanted with both grids and strips, while one subject was implanted with only strips. Overall 9 grids (1 in 4 subjects, 2 in 1 subject, 3 in 1 subject) and 32 strips (range 1-14) for a total of 548 contacts (36 minimum, 92 maximum for each subject) were implanted.

Patients were stabilized post-operatively in the neuro-intensive care unit for approximately 24 hours before being transferred to the epilepsy monitoring unit for intracranial EEG monitoring. Based on the results of intracranial EEG monitoring, two of the subjects had seizures of extra-temporal onset, two of the subjects had seizures of temporal onset, and three of the subjects had seizures of frontal onset.

2.2 Acquisition of CT and MR Images

All subjects had both a post-implant CT and a post-implant MRI. The post-implant spiral CT images (Siemens, Germany) were obtained first, with acquisition time occurring within 12 hours of surgery for all subjects. Both bone and tissue windows were obtained (120 KV, 300 mA, axial slices 1.0 mm thickness).

The post-implant MRI was obtained soon after the initial post-implant CT (range 2-20.3 hours, mean 12.4 hours). The post-implant brain MRI with volumetric sequences was obtained for each subject on a 1.5-T MRI machine (Siemens, Germany) equipped with ultra-gradients, a standard head coil, and vacuum cushion to reduce patient movement. MRI protocol included axial T1 (TE=2.79 ms, TR=1180 ms, FOV=25, flip angle=15°, matrix of 256×256 mm$^2$, 1.0 mm slice thickness); sagittal T1 weighted images (TE=12 ms, TR=410 ms, FOV=23, flip angle=80°, matrix of 256×192 mm$^2$, 5.0 mm slice thickness); axial FLAIR (TE=98 ms, TR=10000 ms, FOV=23, flip angle=150°, matrix of 256×166 mm$^2$, 3.0 mm slice thickness).

2.3 CT and MR Image Alignment

Our fully automated image processing pipeline uses the post-implant CT and post-implant MR images to generate accurate 3D visualization of the intracranial electrodes. In the initial step mutual information is used as the similarity metric to align the post-implant CT and MR images of the same subject. The CT is the floating image and the MR is the fixed image, allowing the CT data to be transformed to the MR space. Rigid and subsequent affine transformations are applied to the CT image to account for the differences of the two brain images in position, rotation and scale. Different transformation parameters of the CT image are probed, resulting in different values in similarity matrices. The transformation corresponding to the maximum value of mutual information is chosen as the best position of the floating image to align with the fixed image. This is a standard method to register multi-modal intra-subject image volumes (Maes et al., 1997).

High intensity electrodes in the CT image are extracted by applying a predefined threshold. Although skull and other bone tissues are brighter than soft brain tissues in CT, metal electrodes are even brighter than most hard tissues. Thresholding may result in extraction of non-electrode objects such as high intensity bone areas and electrode connection wires. The high intensity bone regions are usually small and sparse, and they are removed by the morphological operation of opening, which is morphological erosion (object shrinking) followed by morphological dilation (object expansion). The intensity of the electrode wires outside the brain are similar to the electrode intensity. These eventual artifacts are deleted by applying a brain mask that keeps only electrodes inside or close to the brain. The electrode segmentation is mapped to the MR space by means of the CT to MR image transform obtained previously.

2.4 Brain Parcellation

An external brain atlas with rich cortical annotation is used for segmentation of the subject MR scan. We chose the atlas of Non-rigid Image Registration Evaluation Project (NIREP) from the University of Iowa, which is based on 16 normal adult T1-weighted brain scans and has 32 cortical gray matter labels (Christensen et al., 2006). We added 3 more labels to the NIREP atlas: Subcortical gray matter, white matter, and cerebrospinal fluid. Skull and other non-brain tissues in the subject MR images are stripped by applying the Brain Extraction Tool (Smith, 2002).

The correspondence between the patient MR image and the NIREP atlas is established by non-rigidly registering the gray scale atlas to the patient MR image. The deformation of the registration is diffeomorphic (both forward and backward mappings are smooth) and the registration is symmetric (the mapping from A to B is exactly the inverse of B to A). Cross correlation is used as the similarity metric. The non-rigid registration can overcome the possible local brain deformation and shift resulting from electrode placement or other intervention, even though the atlas used is based on normal healthy brains.

The atlas labels are propagated to the subject MR image through the deformation resulting from the non-rigid registration. In order to further adapt the labels to the patient's anatomy, we perform prior-based segmentation on the subject MR image using the propagated labels as priors (Avants et al., 2011). The segmentation algorithm, called Atropos, adopts a Bayesian framework and finite mixtures to maximize the posterior probability of a set of labels using Expectation Maximization. Atropos can handle a relatively large number of labels such as various cortical subregions with small memory usage. The smoothness of segmentation is enforced by a Markov Random Field component, which encourages each label to be similar to its spatial neighbors on the image grid. Atropos can further refine the resultant brain parcellation to fit the tissue boundary of the MR image. The implementation of the rigid and non-rigid registration, as well as prior-based segmentation are based on the open-source software ANTS (University of Pennsylvania, Philadelphia, Pa.) and its accompanying tools (e.g. Atropos). The non-rigid registration method implemented in ANTS, specifically symmetric normalization (SyN), has been ranked among the most accurate registration methods (Klein et al., 2009).

The three images of the subject CT scan, subject MR scan and label atlas are then normalized in the same space as subject MR scan, resulting in merging of the electrodes with the parcellated brain. The flow chart of the pipeline is shown in FIG. 1. The running time for CT-MR co-registration is approximately 20 minutes for each subject. Brain parcellation takes approximately 3 hours for each MRI.

Figure 10:
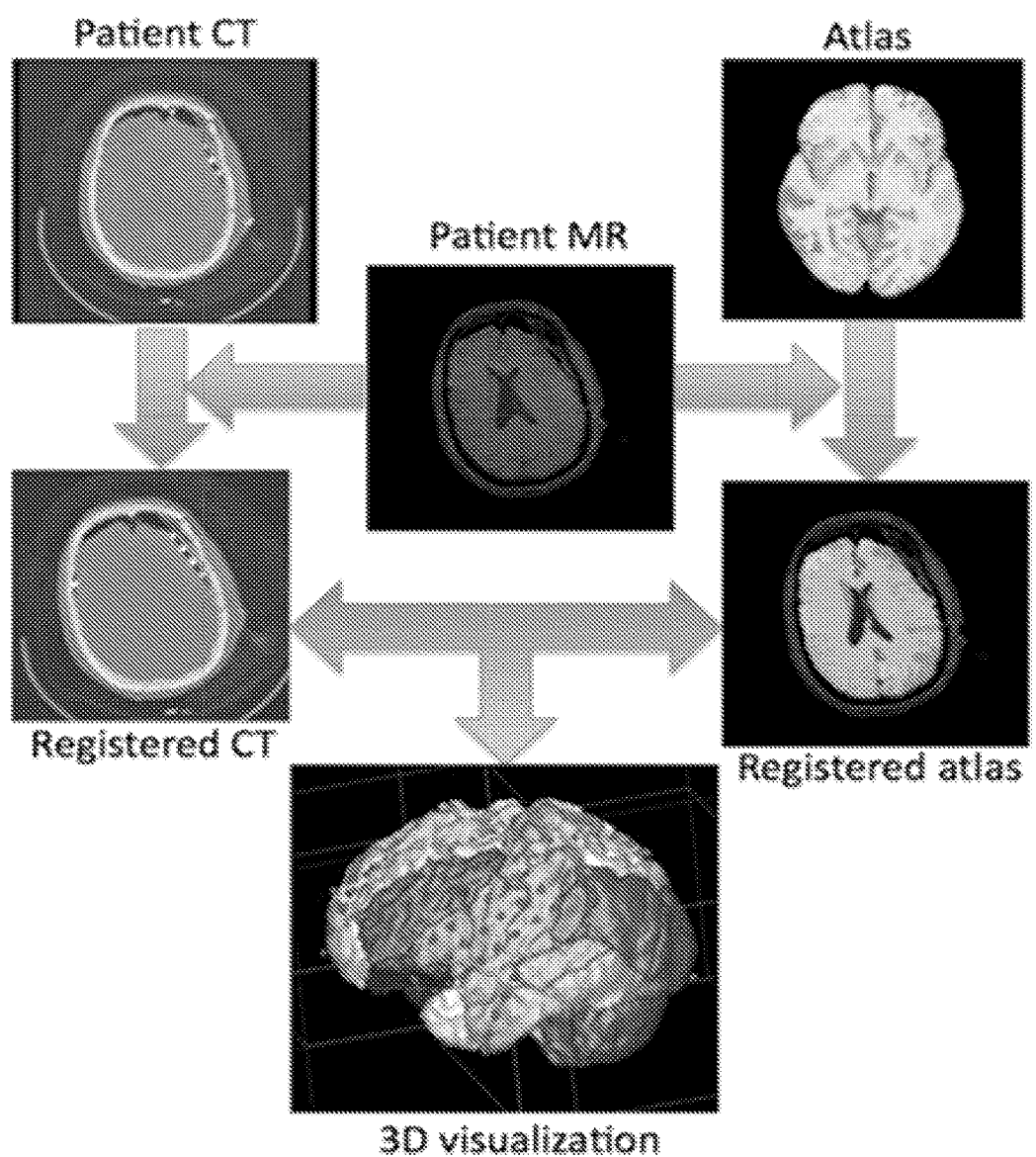
FIG. 10 is a flow chart of a proposed image processing pipeline according to an embodiment of the subject matter described herein.

FIG. 10 is a flow chart of the proposed image processing pipeline. Subject CT (top left) is registered to subject MR image (middle). An external labeled atlas (top right) is also registered to subject MR image. The results of the two registrations are integrated to generate the parcellated brain overlaid with electrodes (bottom).

2.5 Visualization

The resultant electrode and cortical subregion segmentations are visualized in 3D space with distinct colors. The solid segmentations are converted to mesh-based surface representation for efficient manipulation, such as rotation and translation. Smoothing is applied to remove the wavy shape of the segmentations in cases of limited image resolution. Shading is used to provide more realistic 3D rendering. We use the open-source software ITK-SNAP (University of Pennsylvania, Philadelphia, Pa.) for the visualization task. ITK-SNAP includes utility of surface reconstruction and allows simultaneous 3D image rendering and volume navigation (Yushkevich et al., 2006).

In some cases the electrodes in the final segmentation appear partially or fully buried by the brain tissue. We remedy this by using a post-processing script in Matlab (The Mathworks Inc., Natick, Mass.). This script takes as inputs the brain mask produced from the MR and the aligned electrode mask produced from the CT after it is registered to the MR. A ray is projected from the center of the brain to the cortical surface, passing through each individual electrode. The center of mass of each electrode is found and shifted outward along the ray until the center of the electrode reaches the surface. This produces a new electrode mask which is combined with the parcellated brain to create the final output.

2.6 Validation

The alignment between the subject CT and MR images is the core component of the pipeline, allowing for improved visualization of the electrodes with respect to neuroanatomy. To verify the validity of this alignment, we established a protocol to specify the true correspondence between the two image modalities based on anatomical features available in both scans. In the first step of the validation, a single investigator marked 4 identical landmarks on both the post-implant CT and post-implant T1 MRI for all 7 subjects, independent of the co-registration. The landmarks used were the pineal gland, midline inferior most point of the nasal bridge, a frontal cortical point immediately posterior to the superior most midline of the frontal sinus, and the confluence of sinuses with overlap at the internal occipital protuberance. Precise identification of cortical landmarks in the vicinity of electrodes contacts on the MR images could be made, but these same cortical landmarks could not be manually found on the post-implant CT. Post-operative edema as well as metal artifact made identification of these specific cortical points virtually impossible on the post-implant CT. Thus, the above subcortical, bony landmark, and frontal and posterior cortical landmarks were chosen given the feasibility of their segmentation on the post-implant CT. Examples of these marked landmarks for 4 subjects are shown for both the T1 MRI and CT (FIG. 2).

Note that the co-registration algorithm did not use the information from these landmarks and vice versa.

Figure 11:
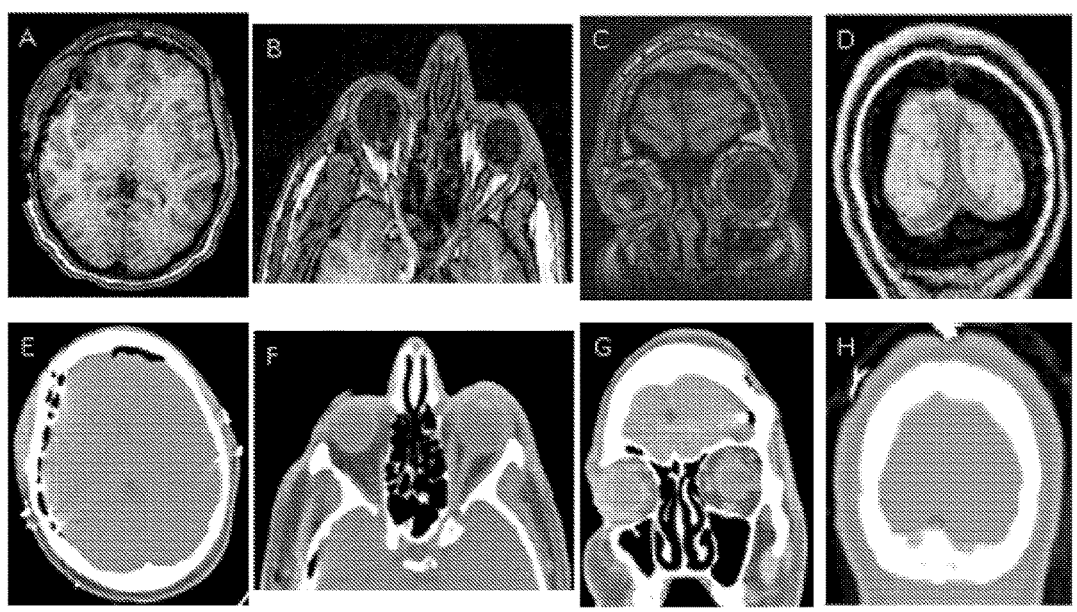
FIG. 11 illustrates images of segmented MRI landmarks of the pineal gland (subject 3, image A), midline inferior most point of the nasal bridge (subject 7, image B), a frontal cortical point immediately posterior to the superior most midline of the frontal sinus (subject 2, image C), and the confluence of sinuses with overlap at the internal occipital protuberance (subject 4, image D). Corresponding CT landmarks for the same subjects (images E-H respectively).

FIG. 11 illustrates images of segmented MRI landmarks of the pineal gland (subject 3, image A), midline inferior most point of the nasal bridge (subject 7, image B), a frontal cortical point immediately posterior to the superior most midline of the frontal sinus (subject 2, image C), and the confluence of sinuses with overlap at the internal occipital protuberance (subject 4, image D). Corresponding CT landmarks for the same subjects (images E-H respectively).

3. Results

The automated pipeline successfully performed rigid registration between the CT and MR images for all 7 subjects, with visualization of all electrode contacts. Even though the intensity atlas was constructed based on normal healthy brains, the non-rigid registration between the subject MR images and the atlas was also successful for all 7 subjects. The post-implant brains were partly deformed due to complications of the craniotomy and subsequent electrode implantation. In addition, epileptic pathology often results in structural changes in the cerebrum. Despite these factors, brain segmentation appeared to produce reasonable partitioning of the cortices, serving as a good reference for electrode localization (FIG. 12).

Figure 12:
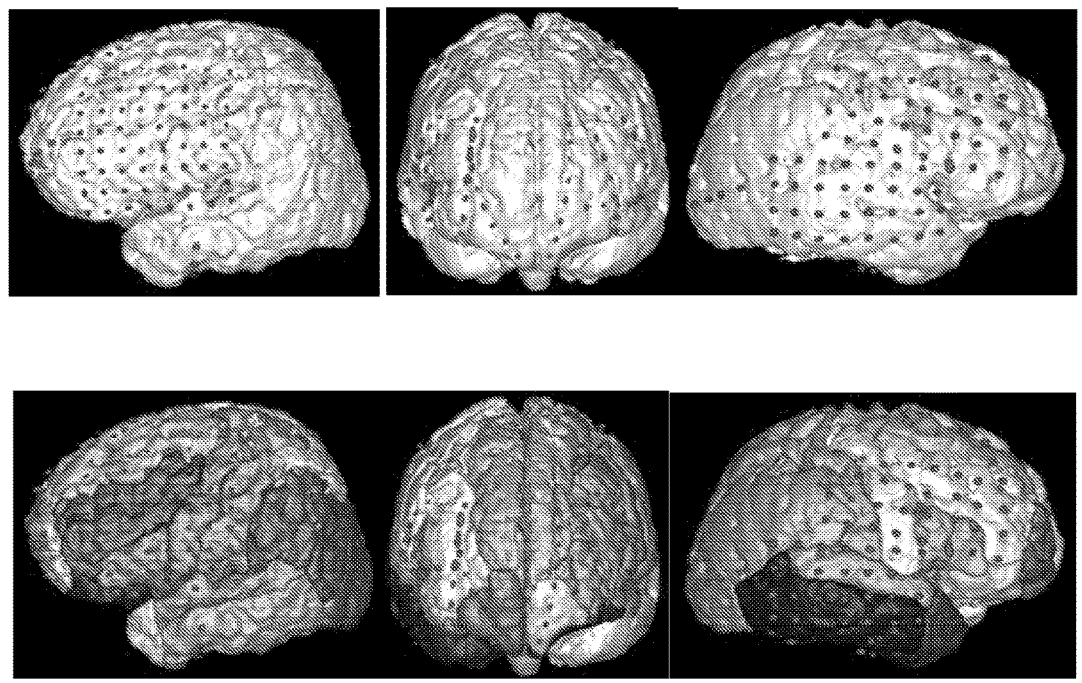
FIG. 12 is a 3D surface visualization of cortices overlaid with electrodes for patients 1, 4 and 3 (left, middle and right columns, respectively). Users can choose either a monochrome brain (first row) or a colored parcellated cortex (second row).

FIG. 12 is a 3D surface visualization of cortices overlaid with electrodes for patients 1, 4 and 3 (left, middle and right columns, respectively). Users can choose either a monochrome brain (first row) or a colored parcellated cortex (second row).

Figure 4:
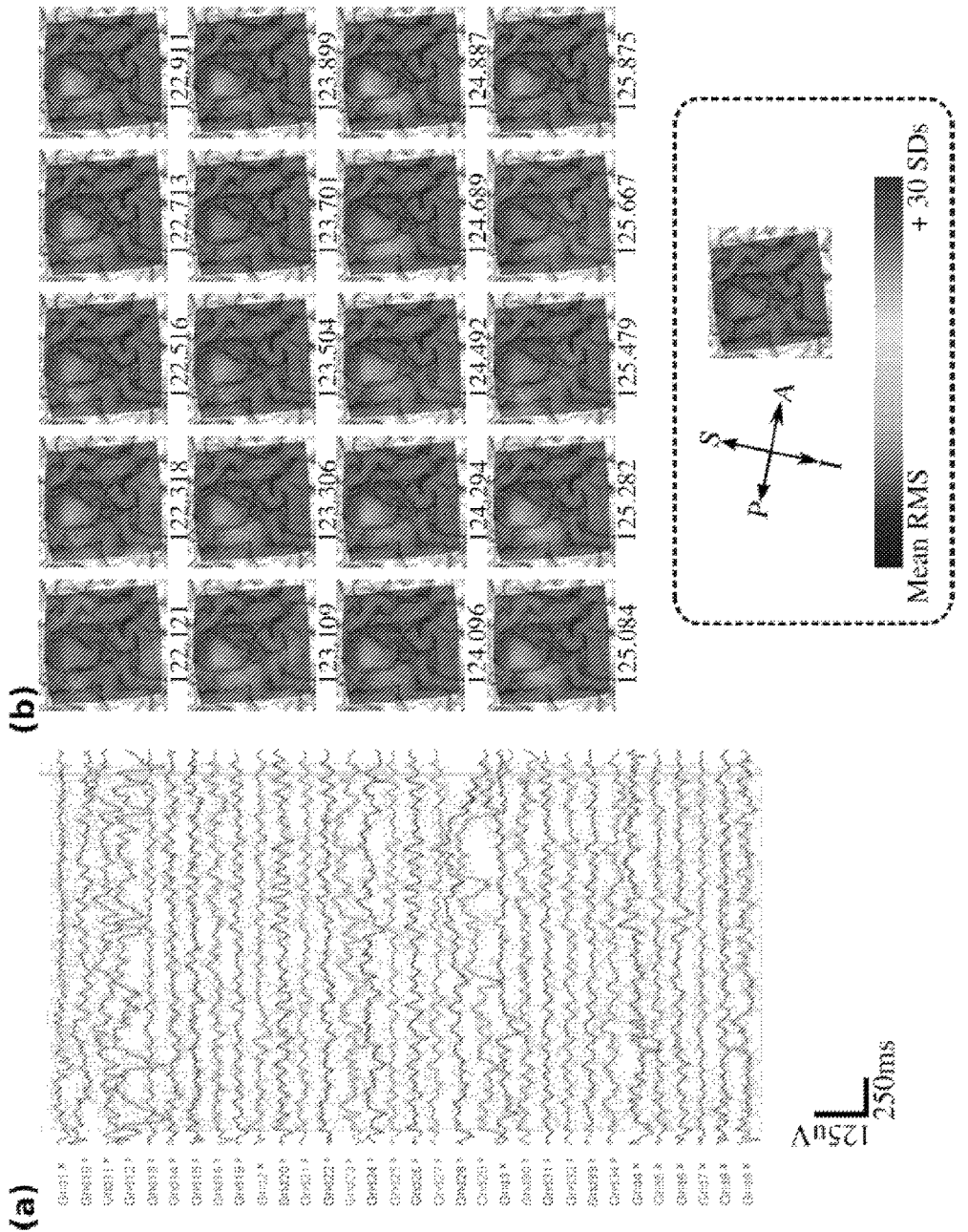
FIG. 4 illustrates preictal HFO initiation and propagation. (a) 4 seconds of EEG beginning 10 seconds prior seizure onset. Visually synchronous activity is seemingly distributed across electrode array. (b) Focal HFO activity coincides with clinican determined SOZ for a duration of 3.7 seconds.

As mentioned in section 2.5, we developed an "excavation" algorithm to correct visualization of buried electrodes. One example result is shown in FIG. 4. This algorithm only needed to be applied to subjects 3 and 7.

Figure 13:
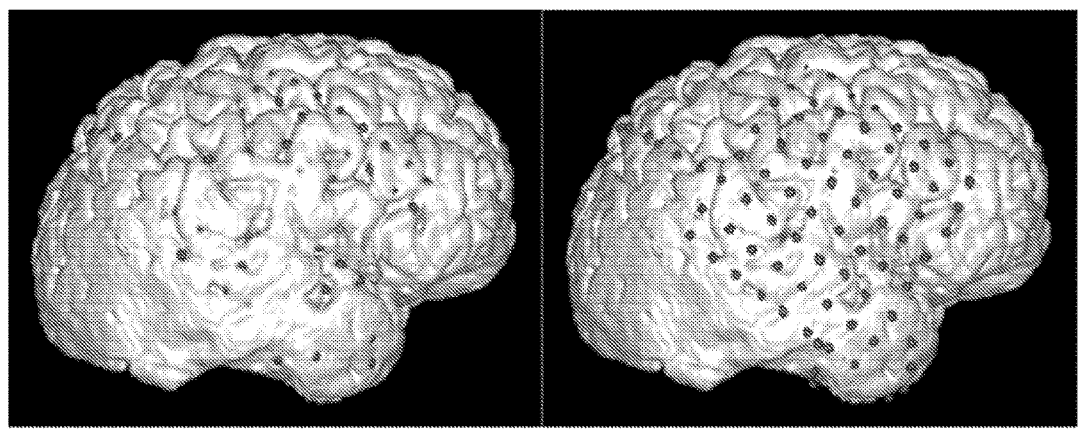
FIG. 13 illustrates the visualization of electrodes on a monochrome brain for subject 7 before (left subfigure) and after (right subfigure) applying the excavation algorithm.

FIG. 13 illustrates the visualization of electrodes on a monochrome brain for subject 7 before (left subfigure) and after (right subfigure) applying the excavation algorithm.

For validation we obtained quantitative results for the accuracy of the alignment between the subject MR and CT. The 3-dimensional coordinates of the segmented masks from the T1 MR images were averaged to locate the center. Following co-registration of the post-implant CT with the post-implant T1 MRI, the same procedure was repeated to calculate the center of the masks on the co-registered CT image. The distance between the centers of the two masks was calculated in a standardized and automated manner. The mean of the distances are as follows: Pineal gland (mean distance, SD) 3.46 mm±1.00 mm, inferior point of nasal bridge 2.08 mm±0.81 mm, frontal cortical point 2.94 mm±1.35 mm, and confluence of sinuses 2.98 mm±1.21 mm. In comparison, the voxel size for all 7 subjects in the X-Y-Z plane was 0.5 mm×0.5 mm×1 mm for the post-implant CT, and 1 mm×1 mm×1 mm for the post-implant T1 MRI. The results of the distances from the center of the masks on the T1 MRI to that of the co-registered CT are shown for all 7 subjects (Table 2).

TABLE 2

Distances (mm) from the center of the masks on the T1 MRI to that of the co-registered CT for all 7 subjects.

| Subject no. | Pineal gland | Nasal bridge | Frontal cortical point | Confluence of sinuses |
|---|---|---|---|---|
| 1 | 4.52 | 3.38 | 1.91 | 2.93 |
| 2 | 4.13 | 2.29 | 3.36 | 3.17 |
| 3 | 2.9 | 2.71 | 4.79 | 2.27 |
| 4 | 1.54 | 1.89 | 1.57 | 4.38 |

TABLE 2-continued

Distances (mm) from the center of the masks on the T1 MRI to that of the co-registered CT for all 7 subjects.

| Subject no. | Pineal gland | Nasal bridge | Frontal cortical point | Confluence of sinuses |
|---|---|---|---|---|
| 5 | 4 | 1.66 | 2.05 | 1.93 |
| 6 | 3.34 | 0.88 | 4.71 | 1.48 |
| 7 | 3.82 | 1.74 | 2.21 | 4.68 |
| Mean | 3.46 ± 1.00 mm | 2.08 ± 0.81 mm | 2.94 ± 1.35 mm | 2.98 ± 1.21 mm |

Nasal bridge represents the midline most inferior point. The frontal cortical point is immediately posterior to the superior most midline of the frontal sinus. The mask for the confluence of sinuses overlaps with the internal occipital protuberance.

4. Discussion

Accurate and clear visualization of intracranial electrodes is essential in the pre-surgical evaluation of epilepsy patients. Such visualization will aid in more precise determination of target regions for resection. This study demonstrates the feasibility of applying a state-of-the-art registration and segmentation method in electrode localization. The practicability of brain parcellation on epileptic brain images after implantation is also demonstrated.

The proposed co-registration method has a high level of validity and effectiveness due to three main advantages. First, it works directly on raw imaging data and is fully automated, meaning that once the input images are provided, manual input or intervention is not necessary. Directly registering raw images with voxel-based whole head (including head and skull) matching does not require complex pre-processing, such as brain surface extraction, skull stripping, or brain tissue segmentation. These pre-processing steps can be error prone, with subsequent propagation of these errors to registration. Second, the MI-based registration is considered to be a gold standard with regard to multi-modal medical image registration with sub-millimeter accuracy due to interpolation between voxels. The adopted implementation (ANTS) has been used and validated by numerous external users. Third, the similarity metric MI is known to be robust to noise or missing and asymmetric information, such as occlusion of brain and electrodes that are visible in the CT image but not in the MRI. One limitation of the co-registration method is that in rare cases it cannot accommodate large discrepancy in head-pose between MR and CT, with optimization being limited to a local optimum; thus resulting in slightly less accurate registration results. The subjects tested in this experiment did not have a large discrepancy in head-pose between MR and CT.

Another reason for the high level of accuracy of our co-registration method was that the post-implant MRI, and not the pre-implant MRI was used for the registration. In many patients with chronic electrode implantation, there is edema as well as subdural blood overlying the electrodes. These factors, along with the thickness of the electrodes and associated hardware can contribute to brain tissue displacement relative to the pre-operative MRI (Dalal et al., 2008). The unequal shift in electrodes renders inaccurate the localization based on mutual cost information algorithms that co-register the post-implant CT with the pre-implant MR (Pieters et al., 2013). Most of the subjects in our study had the post-implant MRI performed soon after (mean of 12.4 hours) the post-implant CT, effectively cancelling most of the effects of brain shift. The majority of other groups employing a co-registration algorithm have only used the pre-implant MRI. This is due to concerns that the final co-registered image will have distortion of anatomical detail in the vicinity of the electrodes if the post-implant MRI is used (Darcey et al., 2010). Results of our final co-registration images for all subjects showed that even with the MRI as the fixed image, the anatomical detail in the vicinity of the electrodes was not compromised.

Due to brain shift as discussed above, other groups employing co-registration of the post-implant CT to the pre-implant MRI have had to devise complicated algorithms to "debury" electrodes on the final 3D co-registered image. This process often adds additional processing time and potentially compromises accuracy. Depth electrodes may also become visible on the cortical surface, making them indistinguishable from subdural electrodes. Even though we used the post-implant MRI for all subjects to minimize the effects of brain shift, we did have to apply a simplified excavation algorithm to 2 of the subjects. It was expected that in these 2 subjects the intervening time period from acquisition of the post-implant MRI from the initial post-implant CT would be above the mean of 12.4 hours (subject 3, 13.75 hours; subject 7, 17 hours), providing enough time for significant brain shift to occur. If the post-implant MRIs were obtained sooner relative to acquisition of the post-implant CT, then the excavation algorithm would not have been needed to be applied.

Compared to other co-registration CT-MRI algorithms, our results of validation are superior or on-par with other groups. Given that the interelectrode distance is usually 10 mm, an error of even 4 mm is substantial and could possibly cause the electrode to be localized on an incorrect gyrus, or possibly the incorrect lobe (Pieters et al., 2013). In the study by Tao et al., four external fiducial markers were used for 3D co-registration of the pre-implant MRI with the post-implant CT. The mean localization error of co-registration compared to intra-operative photographs was 4.3±2.5 mm, with the mean localization error being as high as 6.8±2.4 mm in 6 patients when two or three reliable fiducial markers were used. Other groups also using intraoperative photography as a validation technique have shown comparable results with post-implant CT-MRI co-registration. Sebastiano et al., using brain-surface matching as the 3D CT-MRI co-registration algorithm, carried out validation on all 8 patients studied, with a mean electrode localization error of 2±0.12 mm. Dykstra et al., using a mutual information based transform algorithm, carried out validation on 2 of the 5 patients studied, with a mean electrode localization error of 2.76±0.34 mm.

Our method of validation, with a mean electrode localization error of 2.87±0.58 mm is just as rigorous and with greater accuracy compared to more conventional methods of using intraoperative photographs. The timing of the post-implant CT with respect to when the implantation intra-operative photograph was obtained is not known for the above discussed studies. If there is considerable delay from when the post-implant CT is obtained, then blood and CSF accumulation can occur in the epidural and subdural spaces causing migration of the grid (LaViolette, 2011). It is possible that the grid movement is potentially more than the mean localization error of the electrodes, raising questions with respect to the validation technique of only using an implantation photograph. Using intraoperative photographs also relies heavily on manual inspection of electrodes in reference to anatomical landmarks. Although our method of validation involved manual segmentation of landmarks, the exact same points were found on both the CT and MRI images, with distances between the centers of the masks calculated in an automated fashion. Also, two-dimensional photograph-based distance measures are artificially smaller than the actual three-dimensional distance measures in 3D images. If a line segment is projected in a 3D space to a 2D plane (e.g. a 2D photograph), then the length of the projected line segment will be smaller than the original length based on the Pythagorean theorem.

In contrast to other studies of CT-MRI co-registration that use only implantation photographs as a validation technique, the method of Hermes et al. analyzed grid movement with both implantation and explantation photographs to calculate electrode localization error. They reported a mean electrode localization error of 2.6 mm, but their technique required extra processing time given that pre-implant MR images were used. All electrodes also had to be corrected for brain shift by a more complicated excavation method.

The two recent 3D electrode visualization algorithms developed by Pieters et al. also address the concerns mentioned above with respect to grid shifting and solely using implantation photographs as a validation technique. Similar to work by Hermes et al, they also used implantation and explantation photographs, with substantial grid movement being observed in some of the subjects and incorporated into their validation analysis. This group retested the validity of all prior co-registration algorithms of other groups mentioned here by using their method of intraoperative photograph localization as the gold standard for comparison and testing. Their independent verification results reconfirmed that the CT-MRI co-registration algorithms of other groups were less accurate than ours, with a range of 3.7-4.1 mm. No method of co-registration similar to ours was tested by this group. The recursive grid partitioning method developed by Pieters et al. which also uses intraoperative photographs for co-registration was very accurate, with a mean electrode localization error of 2.0 mm. The robust nature of this algorithm should not be understated, but this technique only works for visualization of grid electrode contacts seen at the surgical field at the time the implantation photograph is taken, with an extrapolation method employed for the remaining non-visible grid electrodes. Subsequently, visualization of strip electrodes on the final 3D image cannot be made. This illustrates that conventional CT-MRI co-registration algorithms serve a critical role in localizing electrodes that are not visible in the surgical field during craniotomy, as is commonly the case when recording from non-convexity cortex such as the temporal lobe (Tao et al., 2009). Our co-registration algorithm did not have this limitation, and our final 3D rendered images clearly showed all electrode contacts for all tested subjects.

This recursive grid partitioning algorithm (Pieters et al., 2013), similar to many other methods, is also semi-automated, requiring the user to manually mark grid corners based on intra-operative photographs. We believe that our technique is superior in being fully automated with increased practicality given its use of common imaging studies that are routinely obtained for most epilepsy patients undergoing surgery with implantation of subdural electrodes. Even with our high level of electrode localization accuracy, a limitation may still be grid movement at the time of explantation, a factor that is not taken into account with post-implant CT-MRI co-registration. In such cases of suspected grid movement, repeat imaging with a CT and a MRI immediately prior to explantation, with subsequent implementation of our proposed co-registration algorithm will eliminate the effects of grid movement on electrode localization error.

Our method also demonstrated brain parcellation on the final 3D co-registered image. Accurate brain parcellation is a challenging task since boundaries between cortical structures are not defined by MRI features, but by prior knowledge or artificial delimitation. Nonetheless, visual inspection showed that the proposed method was able to partition epileptic brains into reasonable subregions. A similar, validated, and semi-automated technique of brain parcellation was recently developed with an unpublished processing time (Pieters et al., 2013). Our method is relatively fast and automated. Using a template with richer annotation can bring finer division of the patient's brain, but more detailed anatomical partitioning remains speculative due to large cortical variation among individuals. Furthermore, the functional anatomy of epilepsy patients may be shifted due to reorganization secondary to epileptogenic networks. This is the main limitation of any parcellation algorithm on epileptic brains; thus, all clinical information gained from these images should only be used in conjunction with results of cortical stimulation mapping.

It will be understood that various details of the subject matter described herein may be changed without departing from the scope of the subject matter described herein. Furthermore, the foregoing description is for the purpose of illustration only, and not for the purpose of limitation.

What is claimed is:

1. A method for visualization of a resection target during epilepsy surgery, the method comprising:
  at a real time neurophysiologic biomarker visualization system stored in a non-transitory computer readable medium and implemented by at least one computer:
    receiving, as input, a pre-electrode-implantation magnetic resonance image (MRI) of an epilepsy patient's brain;
    receiving, as input, a post-electrode-implantation computed tomography (CT) image of the patient's brain;
    receiving, as input, a post-electrode-implantation MRI of the patient's brain;
    receiving, as input, raw EEG data produced by an implanted electrode array, processing the raw EEG data, and generating, in real time, intraoperatively, and from the raw EEG data, spatiotemporal visualizations of occurrences of a neurophysiologic biomarker mapped to locations of the occurrences of the neurophysiologic biomarker, wherein the spatiotemporal visualizations of the occurrences change over time with changes in the raw EEG data and the spatiotemporal visualizations comprise a spatiotemporal color map of results of band-limited, shifting-time-windowed sampling of high frequency oscillations of EEG signals rendered on top of a 3D model of the patient's brain;
    receiving, as input, data identifying a resection target; and
    receiving, as input, coordinates in real space produced by a neuronavigation system;

registering the MRIs, the CT image, the spatiotemporal visualizations of the occurrences of the neurophysiologic biomarker, the data identifying the resection target and the coordinates in real space produced by the neuronavigation system to produce a registered image.

2. The method of claim 1 wherein processing the raw EEG data includes processing the raw EEG data to identify a particular biomarker in the EEG data.

3. The method of claim 1 wherein generating the spatiotemporal visualizations of the occurrences of the neurophysiologic biomarker includes generating a heat map illustrating intensities of the occurrences of the neurophysiologic biomarker mapped to the locations of the occurrences.

4. The method of claim 3 wherein generating the spatiotemporal visualizations includes utilizing color to illustrate relative intensities of the occurrences of the neurophysiologic biomarker.

5. The method of claim 1 wherein the registered image includes an image of the patient's brain, a visual indication of the resection target mapped to the image of the patient's brain, a visualization of occurrence of the neurophysiologic biomarker mapped to the image of the patient's brain, and an image of at least one object tracked by the neuronavigation system mapped to the image of the patient's brain.

6. The method of claim 1 comprising continually receiving the raw EEG data as input and updating the spatiotemporal visualizations of occurrences of the neurophysiologic biomarker mapped to locations of the occurrences.

7. The method of claim 1 wherein outputting the registered image includes outputting the registered image to the neuronavigation for display by the neuronavigation system during epilepsy surgery.

8. A system for visualization of a resection target during epilepsy surgery, the system comprising:
at least one computer; and
a real time neurophysiologic biomarker visualization system stored in a non-transitory computer readable medium, implemented by the at least one computer and configured to:
receive, as input, a pre-electrode-implantation magnetic resonance image (MRI) of an epilepsy patient's brain;
receive, as input, a post-electrode-implantation computed tomography (CT) image of the patient's brain;
receive, as input, a post-electrode-implantation MRI of the patient's brain;
receive, as input, raw EEG data produced by an implanted electrode array, process the raw EEG data, and generate, in real time and intraoperatively, spatiotemporal visualizations of occurrences of a neurophysiologic biomarker mapped to locations of the occurrences of the neurophysiologic biomarker, wherein the spatiotemporal visualizations of the occurrences change over time with changes in the raw EEG data and the spatiotemporal visualizations comprise a spatiotemporal color map of results of band-limited, shifting-time-windowed sampling of high frequency oscillations of EEG signals rendered on top of a 3D model of the patient's brain;
receive, as input, data identifying a resection target; and
receive, as input, coordinates in real space produced by a neuronavigation system;
register the MRIs, the CT image, the spatiotemporal visualizations of the occurrences of the neurophysiologic biomarker, the data identifying the resection target and the coordinates in real space produced by the neuronavigation system to produce a registered image.

9. The system of claim 8 wherein the real time neurophysiologic biomarker visualization system is configured to process the raw EEG data to identify a particular biomarker in the EEG data.

10. The system of claim 8 wherein the real time neurophysiologic biomarker visualization system is configured to generate a heat map illustrating intensities of the occurrences of the neurophysiologic biomarkers mapped to the locations in the image of the patient's brain corresponding to the occurrences.

11. The system of claim 10 wherein the real time neurophysiologic visualization system is configured to utilize color to illustrate relative intensities of the occurrences of the neurophysiologic biomarker.

12. The system of claim 8 wherein the registered image includes an image of the patient's brain, a visual indication of the resection target mapped to the image of the patient's brain, a visualization of occurrence of the neurophysiologic biomarker mapped to the image of the patient's brain, and an image of at least one object tracked by the neuronavigation system mapped to the image of the patient's brain.

13. The system of claim 8 wherein the real time neurophysiologic biomarker visualization system is configured to receive the raw EEG data as input and to update the spatiotemporal visualizations of occurrences of the neurophysiologic biomarker mapped to locations of the occurrences.

14. The system of claim 8 wherein the real time neurophysiologic biomarker visualization system is configured to output the registered image to the neuronavigation system for display by the neuronavigation system during epilepsy surgery.

15. A non-transitory computer readable medium having stored thereon executable instructions that when executed by a processor of a computer control the computer to perform steps comprising:
at a real time neurophysiologic biomarker visualization system embodied in the non-transitory computer readable medium and implemented by the computer:
receiving, as input, a pre-electrode-implantation magnetic resonance image (MRI) of an epilepsy patient's brain;
receiving, as input, a post-electrode-implantation computed tomography (CT) image of the patient's brain;
receiving, as input, a post-electrode-implantation MRI of the patient's brain;
receiving, as input, raw EEG data produced by an implanted electrode array, processing the raw EEG data, and generating, in real time, intraoperatively, and from the raw EEG data, spatiotemporal visualizations of occurrences of a neurophysiologic biomarker mapped to locations of the occurrences of the neurophysiologic biomarker, wherein the spatiotemporal visualizations change over time with changes in the raw EEG data and the spatiotemporal visualizations comprise a spatiotemporal color map of results of band-limited, shifting-time-windowed sampling of high frequency oscillations of EEG signals rendered on top of a 3D model of the patient's brain;
receiving, as input, data identifying a resection target; and
receiving, as input, coordinates in real space produced by a neuronavigation system;
registering the MRIs, the CT image, the spatiotemporal visualizations of the occurrences of the neurophysiologic biomarker, the data identifying the resection target and the coordinates in real space produced by the neuronavigation system to produce a registered image.

16. A method for real time spatiotemporal visualization of neurophysiologic biomarkers, the method comprising:
receiving, at a computational engine implemented by at least one computer, raw data collected from a cortical electrode array;
processing the raw data to generate data indicative of occurrences of a neurophysiologic biomarker;
generating, intraoperatively, spatiotemporal visualizations of the processed data that maps the occurrences of the neurophysiologic biomarker to its spatial origins in two-dimensions or to locations in an image of at least a portion of a patient's brain corresponding to the occurrences in three-dimensions, wherein the spatiotemporal visualizations change over time with changes in the raw data collected by the cortical electrode array and the spatiotemporal visualizations comprise a spatiotemporal color map of results of band-limited, shifting-time-windowed sampling of high frequency oscillations of EEG signals rendered on top of a 3D model of the patient's brain; and
outputting the spatiotemporal visualizations to a user, wherein the processing, generating, and outputting are performed in real time.

17. The method of claim 16 wherein receiving raw data collected from a cortical electrode array includes receiving neurophysiologic recordings collected from intracranial, extracranial, or spinal electrodes applied to a patient for the purpose of diagnosis or administration of therapy.

18. The method of claim 17 wherein processing the raw data to generate data indicative of occurrences of a neurophysiologic biomarker includes processing the raw data to identify a particular biomarker in the recorded data.

19. The method of claim 16 wherein processing the raw data to generate data indicative of the occurrences of the neurophysiologic biomarker includes processing the data using a neurophysiologic biomarker specific plugin to the computational engine for identifying a neurophysiologic biomarker.

20. The method of claim 16 wherein generating the spatiotemporal visualizations of the processed data includes generating a heat map illustrating intensities of the occurrences of the neurophysiologic biomarker mapped to the image of the relevant location or locations within the neuroaxis.

21. The method of claim 20 wherein generating the spatiotemporal visualizations includes continually updating the heat map as the occurrences of the neurophysiologic biomarker change over time.

22. The method of claim 20 wherein generating the spatiotemporal visualizations includes utilizing color to illustrate relative intensities of the occurrences of the neurophysiologic biomarker.

23. The method of claim 16 wherein performing the processing, generating, and outputting in real time includes performing the processing, generating, and outputting during intracranial electrode implantation to provide real time visual feedback of neurophysiological biomarker generation site locations with respect to placement locations of an intracranial or spinal electrode.

24. The method of claim 16 wherein performing the processing, generating, and outputting in real time includes performing the processing, generating, and outputting during invasive monitoring of neurophysiological biomarker generation to identify a target volume in the patient's brain or spinal cord for targeted therapy.

25. The method of claim 16 wherein performing the processing, generating, and outputting in real time includes performing the processing, generating, and outputting during surgical interventions to identify neurophysiologic properties to verify a surgical target.

26. A system for real time spatiotemporal visualization of neurophysiologic biomarkers, the system comprising:
at least one computer;
a computational engine implemented by the at least one computer and configured to receive raw data collected from a cortical electrode array, to process the raw data to generate data indicative of occurrences of a neurophysiologic biomarker; and
a graphical user interface configured to receive the processed data and to generate, intraoperatively, spatiotemporal visualizations of the processed data that maps occurrences of the neurophysiologic biomarker to its spatial origins in two dimensions or to locations in an image of at least a portion of a patient's brain corresponding to the occurrences in three dimensions and for outputting the spatiotemporal visualizations to a user, wherein the processing, generating, and outputting are performed in real time and, wherein the spatiotemporal visualizations change over time with changes in the raw data collected by the cortical electrode array and the spatiotemporal visualizations comprise a spatiotemporal color map of results of band-limited, shifting-time-windowed sampling of high frequency oscillations of EEG signals rendered on top of a 3D model of the patient's brain.

27. The system of claim 26 wherein the computational engine is configured to receive neurophysiologic recordings collected from intracranial, extracranial, or spinal electrodes applied to a patient for the purpose of diagnosis or administration of therapy.

28. The system of claim 27 the computational engine is configured to process the raw data to identify a particular biomarker in the neurophysiologic recordings.

29. The system of claim 26 wherein the computational engine is configured with a neurophysiologic biomarker specific plugin for identifying the neurophysiologic biomarker.

30. The system of claim 26 wherein the graphical user interface is configured to generate a heat map illustrating intensities of the occurrences of the neurophysiologic biomarkers mapped to the locations in the image of the patient's brain or spinal cord corresponding to the occurrences.

31. The system of claim 30 wherein the graphical user interface is configured to continually update the heat map as the occurrences of the neurophysiologic biomarker change over time.

32. The system of claim 30 wherein the graphical user interface is configured to utilize color to illustrate relative intensities of the occurrences of the neurophysiologic biomarker.

33. The system of claim 26 wherein the computational engine is configured to perform the processing and the graphical user interface is configured to perform the generating and the outputting during intracranial electrode implantation to provide real time visual feedback of neurophysiological biomarker generation site locations with respect to placement locations of an intracranial, extracranial, or spinal electrode array.

34. The system of claim 26 wherein the computational engine is configured to perform the processing and the graphical user interface is configured to perform the generating and the outputting during invasive monitoring of neurophysiological biomarker generation to identify a target volume in the patient's brain or spinal cord for targeted therapy.

35. The system of claim 26 wherein the computational engine is configured to perform the processing and the graphical user interface is configured to performing the processing, generating, and outputting during surgical interventions to identify neurophysiologic properties to verify a surgical target.

36. A non-transitory computer readable medium having stored thereon executable instructions that when executed by a processor of a computer control the computer to perform steps comprising:

receiving, at a computational engine implemented by the computer, raw data collected from a cortical electrode array;

processing the raw data to generate data indicative of occurrences of a neurophysiologic biomarker;

generating, intraoperatively, spatiotemporal visualizations of the processed data that maps occurrences of the neurophysiologic biomarker to its spatial origins in two dimensions or locations in an image of at least a portion of a patient's brain corresponding to the occurrences in three dimensions, wherein the spatiotemporal visualizations change over time with changes in the raw data collected by the cortical electrode array and the spatiotemporal visualizations comprise a spatiotemporal color map of results of band-limited, shifting-time-windowed sampling of high frequency oscillations of EEG signals rendered on top of a 3D model of the patient's brain; and outputting the spatiotemporal visualizations to a user, wherein the processing, generating, and outputting are performed in real time.

* * * * *